(12) United States Patent
Casillas et al.

(10) Patent No.: US 12,332,128 B2
(45) Date of Patent: *Jun. 17, 2025

(54) APPAREL HAVING SENSOR SYSTEM

(71) Applicant: NIKE, Inc., Beaverton, OR (US)

(72) Inventors: Tina M. Casillas, Portland, OR (US); James C. Meschter, Portland, OR (US); Richard L. Watkins, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/608,567

(22) Filed: Mar. 18, 2024

(65) Prior Publication Data

US 2024/0255364 A1   Aug. 1, 2024

Related U.S. Application Data

(63) Continuation of application No. 17/702,365, filed on Mar. 23, 2022, now Pat. No. 11,946,818, which is a
(Continued)

(51) Int. Cl.
*G01L 1/20* (2006.01)
*A41D 1/00* (2018.01)
(Continued)

(52) U.S. Cl.
CPC ............ *G01L 1/205* (2013.01); *A61B 5/1126* (2013.01); *A61B 5/6802* (2013.01);
(Continued)

(58) Field of Classification Search
CPC ..... G01L 1/205; A61B 5/1126; A61B 5/6802; A61B 5/6804; A61B 5/6805; A61B 5/002;
(Continued)

(56) References Cited

U.S. PATENT DOCUMENTS 4,518,267 A   5/1985  Hepp
4,578,769 A   3/1986  Frederick
(Continued)

FOREIGN PATENT DOCUMENTS

CN   1136789 A   11/1996
CN   1746643 A    3/2006
(Continued)

OTHER PUBLICATIONS

Dec. 11, 2009—(WO) ISR & WO—App. No. PCT/US09/047246
(Continued)

*Primary Examiner* — Pierre E Elisca
(74) *Attorney, Agent, or Firm* — Banner & Witcoff, Ltd.

(57) ABSTRACT

An athletic performance monitoring system includes an article of apparel having a upper body portion and a lower body portion, a sensor system configured to sense a movement of the user and including an upper body sensor connected to the upper body portion, a lower body sensor connected to the lower body portion, at least one port in communication with the sensors, and a plurality of conductive leads connecting the sensors to the port(s). The sensors may be stretch-based sensors that increase in resistance upon tensile deformation. At least one electronic module is connected to the port(s) to collect movement data from the sensors through the port(s). The module(s) may analyze the movement data and provide real-time feedback to the user regarding the movement of the user, based on analysis of the movement data, or the module(s) may transmit the movement data to an external device for analysis.

20 Claims, 15 Drawing Sheets

Related U.S. Application Data continuation of application No. 16/919,347, filed on Jul. 2, 2020, now Pat. No. 11,320,325, which is a continuation of application No. 16/195,109, filed on Nov. 19, 2018, now Pat. No. 10,704,966, which is a continuation of application No. 15/824,593, filed on Nov. 28, 2017, now Pat. No. 10,139,293, which is a continuation of application No. 14/702,299, filed on May 1, 2015, now Pat. No. 9,841,330, which is a continuation of application No. 13/713,967, filed on Dec. 13, 2012, now Pat. No. 9,043,004.

(51) Int. Cl.
- *A61B 5/00* (2006.01)
- *A61B 5/11* (2006.01)
- *A63B 24/00* (2006.01)

(52) U.S. Cl.
CPC .......... *A61B 5/6804* (2013.01); *A61B 5/6805* (2013.01); *A63B 24/00* (2013.01); *A41D 1/002* (2013.01); *A61B 5/002* (2013.01); *A61B 5/1114* (2013.01); *A61B 2503/10* (2013.01); *A61B 2562/0261* (2013.01); *A61B 2562/04* (2013.01)

(58) Field of Classification Search
CPC .............. A61B 5/1114; A61B 2503/10; A61B 2562/0261; A61B 2562/04; A63B 24/00; A41D 1/002
USPC .......................................................... 700/91
See application file for complete search history.

(56) References Cited

U.S. PATENT DOCUMENTS

| | | |
|---|---|---|
| 4,647,918 A | 3/1987 | Goforth |
| 4,715,235 A | 12/1987 | Fukui et al. |
| 4,745,930 A | 5/1988 | Confer |
| 4,866,412 A | 9/1989 | Rzepczynski |
| 5,047,952 A | 9/1991 | Kramer et al. |
| 5,100,713 A | 3/1992 | Homma et al. |
| 5,150,536 A | 9/1992 | Strong |
| 5,280,265 A | 1/1994 | Kramer et al. |
| 5,368,042 A | 11/1994 | O'Neal et al. |
| 5,373,651 A | 12/1994 | Wood |
| 5,422,521 A | 6/1995 | Neer et al. |
| 5,444,462 A | 8/1995 | Wambach |
| 5,471,405 A | 11/1995 | Marsh |
| 5,636,146 A | 6/1997 | Flentov et al. |
| 5,636,378 A | 6/1997 | Griffith |
| 5,638,300 A | 6/1997 | Johnson |
| 5,702,323 A | 12/1997 | Poulton |
| 5,785,666 A | 7/1998 | Costello et al. |
| 5,813,142 A | 9/1998 | Demon |
| 5,813,406 A | 9/1998 | Kramer et al. |
| 5,844,861 A | 12/1998 | Maurer |
| 5,903,454 A | 5/1999 | Hoffberg et al. |
| 5,906,004 A | 5/1999 | Lebby et al. |
| 5,907,819 A | 5/1999 | Johnson |
| 5,913,727 A | 6/1999 | Ahdoot |
| 5,929,332 A | 7/1999 | Brown |
| 5,960,380 A | 9/1999 | Flentov et al. |
| 5,963,891 A | 10/1999 | Walker et al. |
| 6,001,749 A | 12/1999 | Child et al. |
| 6,018,705 A | 1/2000 | Gaudet et al. |
| 6,047,203 A | 4/2000 | Sackner et al. |
| 6,050,962 A | 4/2000 | Kramer et al. |
| 6,066,075 A | 5/2000 | Poulton |
| 6,081,750 A | 6/2000 | Hoffberg et al. |
| 6,110,130 A | 8/2000 | Kramer |
| 6,122,340 A | 9/2000 | Darley et al. |
| 6,145,551 A | 11/2000 | Jayaraman et al. |
| 6,174,294 B1 | 1/2001 | Crabb et al. |
| 6,195,921 B1 | 3/2001 | Truong |
| 6,198,394 B1 | 3/2001 | Jacobsen et al. |
| 6,266,623 B1 | 7/2001 | Vock et al. |
| 6,298,314 B1 | 10/2001 | Blackadar et al. |
| 6,336,365 B1 | 1/2002 | Blackadar et al. |
| 6,341,504 B1 | 1/2002 | Istook |
| 6,357,147 B1 | 3/2002 | Darley et al. |
| 6,374,643 B2 | 4/2002 | Orima |
| 6,381,482 B1 | 4/2002 | Jayaraman et al. |
| 6,428,490 B1 | 8/2002 | Kramer et al. |
| 6,430,843 B1 | 8/2002 | Potter et al. |
| 6,493,652 B1 | 12/2002 | Ohlenbusch et al. |
| 6,496,787 B1 | 12/2002 | Flentov et al. |
| 6,498,994 B2 | 12/2002 | Vock et al. |
| 6,516,284 B2 | 2/2003 | Flentov et al. |
| 6,536,139 B2 | 3/2003 | Darley et al. |
| 6,539,336 B1 | 3/2003 | Vock et al. |
| 6,560,903 B1 | 5/2003 | Darley |
| 6,578,291 B2 | 6/2003 | Hirsch et al. |
| 6,611,789 B1 | 8/2003 | Darley |
| 6,640,144 B1 | 10/2003 | Huang et al. |
| 6,668,380 B2 | 12/2003 | Marmaropoulos et al. |
| 6,718,200 B2 | 4/2004 | Marmaropoulos et al. |
| 6,727,197 B1 | 4/2004 | Wilson et al. |
| 6,748,462 B2 | 6/2004 | Dubil et al. |
| 6,785,579 B2 | 8/2004 | Huang et al. |
| 6,785,805 B1 | 8/2004 | House et al. |
| 6,808,462 B2 | 10/2004 | Snyder et al. |
| 6,829,512 B2 | 12/2004 | Huang et al. |
| 6,836,744 B1 | 12/2004 | Asphahani et al. |
| 6,854,296 B1 | 2/2005 | Miller, III |
| 6,882,897 B1 | 4/2005 | Fernandez |
| 6,889,282 B2 | 5/2005 | Schollenberger |
| 6,892,216 B2 | 5/2005 | Coburn, II et al. |
| 6,909,420 B1 | 6/2005 | Nicolas et al. |
| 6,922,664 B1 | 7/2005 | Fernandez et al. |
| 6,941,775 B2 | 9/2005 | Sharma |
| 6,959,259 B2 | 10/2005 | Vock et al. |
| 6,963,818 B2 | 11/2005 | Flentov et al. |
| 6,978,320 B2 | 12/2005 | Nonaka |
| 7,046,151 B2 | 5/2006 | Dundon |
| 7,054,784 B2 | 5/2006 | Flentov et al. |
| 7,070,571 B2 | 7/2006 | Kramer et al. |
| 7,092,846 B2 | 8/2006 | Vock et al. |
| 7,135,227 B2 | 11/2006 | Karayianni et al. |
| 7,152,343 B2 | 12/2006 | Whatley |
| 7,171,331 B2 | 1/2007 | Vock et al. |
| 7,173,437 B2 | 2/2007 | Hervieux et al. |
| 7,200,517 B2 | 4/2007 | Darley et al. |
| 7,245,898 B2 | 7/2007 | Van Bosch et al. |
| 7,277,021 B2 | 10/2007 | Beebe et al. |
| 7,304,580 B2 | 12/2007 | Sullivan et al. |
| 7,306,403 B1 | 12/2007 | Sanders |
| 7,320,947 B2 | 1/2008 | Child et al. |
| 7,348,285 B2 | 3/2008 | Dhawan et al. |
| 7,365,031 B2 | 4/2008 | Swallow et al. |
| 7,428,471 B2 | 9/2008 | Darley et al. |
| 7,433,805 B2 | 10/2008 | Vock et al. |
| 7,457,724 B2 | 11/2008 | Vock et al. |
| 7,498,956 B2 | 3/2009 | Baier et al. |
| 7,522,970 B2 | 4/2009 | Fernandez |
| 7,559,902 B2 | 7/2009 | Ting et al. |
| 7,579,946 B2 | 8/2009 | Case, Jr. |
| 7,592,276 B2 | 9/2009 | Hill et al. |
| 7,607,243 B2 | 10/2009 | Berner, Jr. et al. |
| 7,617,068 B2 | 11/2009 | Tadin et al. |
| 7,623,987 B2 | 11/2009 | Vock et al. |
| 7,635,439 B2 | 12/2009 | Child et al. |
| 8,251,930 B2 | 8/2012 | Ido |
| 8,474,153 B2 | 7/2013 | Brie et al. |
| 2002/0169387 A1 | 11/2002 | Marmaropoulos et al. |
| 2003/0009308 A1 | 1/2003 | Kirtley |
| 2003/0163287 A1 | 8/2003 | Vock et al. |
| 2003/0181832 A1 | 9/2003 | Carnahan et al. |
| 2004/0051082 A1 | 3/2004 | Child et al. |
| 2004/0087228 A1 | 5/2004 | Van Heerden et al. |
| 2004/0226192 A1 | 11/2004 | Geer et al. |
| 2005/0032582 A1 | 2/2005 | Mahajan et al. |
| 2005/0034485 A1 | 2/2005 | Klefstad-Sillonville et al. |

(56) References Cited

U.S. PATENT DOCUMENTS

| | | | |
|---|---|---|---|
| 2005/0081913 A1 | 4/2005 | Ebbesen et al. | |
| 2005/0095406 A1 | 5/2005 | Gunzel et al. | |
| 2005/0096513 A1 | 5/2005 | Ozguz et al. | |
| 2005/0106977 A1 | 5/2005 | Coulston | |
| 2005/0183292 A1 | 8/2005 | DiBenedetto et al. | |
| 2005/0221403 A1 | 10/2005 | Gazenko | |
| 2005/0282633 A1 | 12/2005 | Nicolas et al. | |
| 2006/0010174 A1 | 1/2006 | Nguyen et al. | |
| 2006/0017692 A1 | 1/2006 | Wehrenberg et al. | |
| 2006/0025229 A1 | 2/2006 | Mahajan et al. | |
| 2006/0094948 A1 | 5/2006 | Gough et al. | |
| 2006/0122528 A1 | 6/2006 | Gal | |
| 2006/0143645 A1 | 6/2006 | Vock et al. | |
| 2006/0144152 A1 | 7/2006 | Cabuz et al. | |
| 2006/0248749 A1 | 11/2006 | Ellis | |
| 2006/0262120 A1 | 11/2006 | Rosenberg | |
| 2007/0006489 A1 | 1/2007 | Case et al. | |
| 2007/0021269 A1 | 1/2007 | Shum | |
| 2007/0032748 A1 | 2/2007 | McNeil et al. | |
| 2007/0038057 A1 | 2/2007 | Nam et al. | |
| 2007/0063849 A1 | 3/2007 | Rosella et al. | |
| 2007/0063850 A1 | 3/2007 | Devaul et al. | |
| 2007/0067885 A1 | 3/2007 | Fernandez | |
| 2007/0068244 A1 | 3/2007 | Billing et al. | |
| 2007/0078324 A1 | 4/2007 | Wijisiriwardana | |
| 2007/0130676 A1 | 6/2007 | Von Blucher | |
| 2007/0143452 A1 | 6/2007 | Suenbuel et al. | |
| 2007/0152812 A1 | 7/2007 | Wong et al. | |
| 2007/0173705 A1 | 7/2007 | Teller et al. | |
| 2007/0250286 A1 | 10/2007 | Duncan et al. | |
| 2007/0260421 A1 | 11/2007 | Berner et al. | |
| 2007/0283599 A1 | 12/2007 | Talbott | |
| 2007/0293750 A1 | 12/2007 | Kuo et al. | |
| 2007/0299325 A1 | 12/2007 | Farrell et al. | |
| 2008/0027679 A1 | 1/2008 | Shklarski | |
| 2008/0028783 A1 | 2/2008 | Immel et al. | |
| 2008/0056508 A1 | 3/2008 | Pierce et al. | |
| 2008/0066343 A1 | 3/2008 | Sanabria-Hernandez | |
| 2008/0091097 A1 | 4/2008 | Linti et al. | |
| 2008/0093687 A1 | 4/2008 | Antaki | |
| 2008/0127527 A1 | 6/2008 | Chen | |
| 2008/0172498 A1 | 7/2008 | Boucard | |
| 2008/0177507 A1 | 7/2008 | Mian et al. | |
| 2008/0203144 A1 | 8/2008 | Kim | |
| 2008/0228097 A1 | 9/2008 | Tang et al. | |
| 2008/0246629 A1 | 10/2008 | Tsui et al. | |
| 2008/0255794 A1 | 10/2008 | Levine | |
| 2008/0256691 A1 | 10/2008 | White et al. | |
| 2008/0259028 A1 | 10/2008 | Teepell et al. | |
| 2008/0287769 A1 | 11/2008 | Kurzweil et al. | |
| 2008/0306410 A1 | 12/2008 | Kalpaxis et al. | |
| 2008/0318679 A1 | 12/2008 | Tran et al. | |
| 2009/0018691 A1 | 1/2009 | Fernandez | |
| 2009/0047481 A1 | 2/2009 | Welsch et al. | |
| 2009/0048538 A1 | 2/2009 | Levine et al. | |
| 2009/0049871 A1 | 2/2009 | Klett et al. | |
| 2009/0053950 A1 | 2/2009 | Surve | |
| 2009/0095094 A1 | 4/2009 | Helmer et al. | |
| 2009/0105047 A1 | 4/2009 | Guidi et al. | |
| 2009/0107009 A1 | 4/2009 | Bishop et al. | |
| 2009/0112078 A1 | 4/2009 | Tabe | |
| 2009/0137933 A1 | 5/2009 | Lieberman et al. | |
| 2009/0153369 A1 | 6/2009 | Baier et al. | |
| 2009/0153477 A1 | 6/2009 | Saenz | |
| 2009/0167677 A1 | 7/2009 | Kruse et al. | |
| 2009/0171188 A1* | 7/2009 | Paul | G01R 33/287 |
| | | | 600/422 |
| 2010/0004566 A1 | 1/2010 | Son et al. | |
| 2010/0010379 A1 | 1/2010 | De Rossi et al. | |
| 2010/0077528 A1 | 4/2010 | Lind et al. | |
| 2010/0267883 A1* | 10/2010 | Bhatt | C08J 5/005 |
| | | | 524/495 |
| 2012/0202397 A1* | 8/2012 | Wolf | H01B 1/24 |
| | | | 977/932 |
| 2012/0291563 A1 | 11/2012 | Schrock et al. | |
| 2016/0219968 A1* | 8/2016 | Martin | A61B 5/221 |
| 2017/0127753 A1* | 5/2017 | Kohatsu | A43B 7/142 |

FOREIGN PATENT DOCUMENTS

| | | |
|---|---|---|
| CN | 101583403 A | 11/2009 |
| CN | 101890215 A | 11/2010 |
| CN | 102727182 A | 10/2012 |
| CN | 102781319 A | 11/2012 |
| EP | 1707065 A1 | 10/2006 |
| EP | 1901048 A2 | 3/2008 |
| EP | 2505090 A2 | 10/2012 |
| GB | 251054 A | 4/1926 |
| GB | 2421416 A | 6/2006 |
| JP | S6114501 A | 1/1986 |
| JP | S61200403 A | 9/1986 |
| JP | S6470783 A | 3/1989 |
| JP | 09159402 A | 6/1997 |
| JP | 2005127828 A | 5/2005 |
| JP | 2005156531 A | 6/2005 |
| JP | 2005270640 A | 10/2005 |
| JP | 2005350614 A | 12/2005 |
| JP | 200675456 A | 3/2006 |
| JP | 200715117 A | 1/2007 |
| JP | 200775172 A | 3/2007 |
| JP | 2007533109 A | 11/2007 |
| JP | 2008503287 A | 2/2008 |
| JP | 2008504856 A | 2/2008 |
| JP | 2009502325 A | 1/2009 |
| JP | 2010246678 A | 11/2010 |
| JP | 2011524207 A | 9/2011 |
| JP | 2012107924 A | 6/2012 |
| JP | 2012139493 A | 7/2012 |
| JP | 2012188799 A | 10/2012 |
| JP | 2012214968 A | 11/2012 |
| WO | 2005117030 A2 | 12/2005 |
| WO | 2007064735 A2 | 6/2007 |
| WO | 2008061023 A2 | 5/2008 |
| WO | 2009152456 A2 | 12/2009 |
| WO | 2011026257 A1 | 3/2011 |
| WO | 2012082782 A1 | 6/2012 |
| WO | 2012112931 A2 | 8/2012 |
| WO | 2012143274 A2 | 10/2012 |

OTHER PUBLICATIONS

Sep. 25, 2012—(WO) ISR & WO—App. No. PCT/US12/025713.
Aug. 21, 2012—(WO) ISR & WO—App. No. PCT/US12/025717.
Aug. 20, 2013—(WO) IPRP—App. No. PCT/US12/025713.
May 28, 2013—(WO) ISR & WO—App. No. PCT/US13/027421.
Aug. 7, 2013—(WO) ISR—App. No. PCT/US13/027397.
Jul. 11, 2012—(WO) ISR & WO—App. No. PCT/US12/025709.
Morris, Stacy, J., A Shoe-Integrated Sensor System for Wireless Gait Analysis and Real-Time Therapeutic Feedback, dissertation, 2004, pp. 1-314, Massachusetts Institute of Technology, MA.
Jul. 30, 2014—(WO) ISR—App No. PCT/US2013/075130.
Aug. 25, 2017—(EP) ESR—App. No. 171664170.0.
Aug. 23, 2019—(EP) ESR—App. No. 19171023.5.
Oct. 19, 2022—(EP) ESR—App. No. 22183238.9.

* cited by examiner

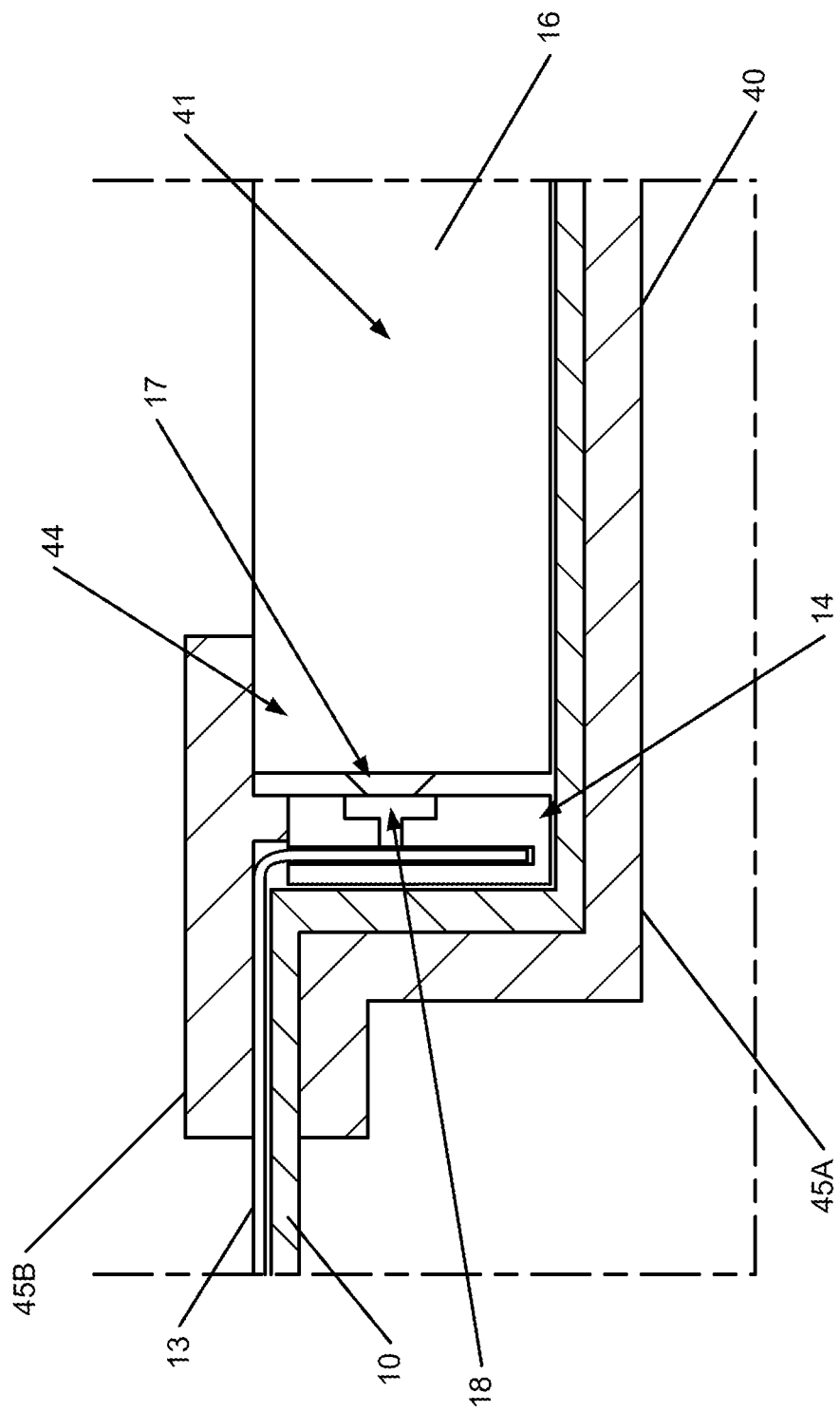

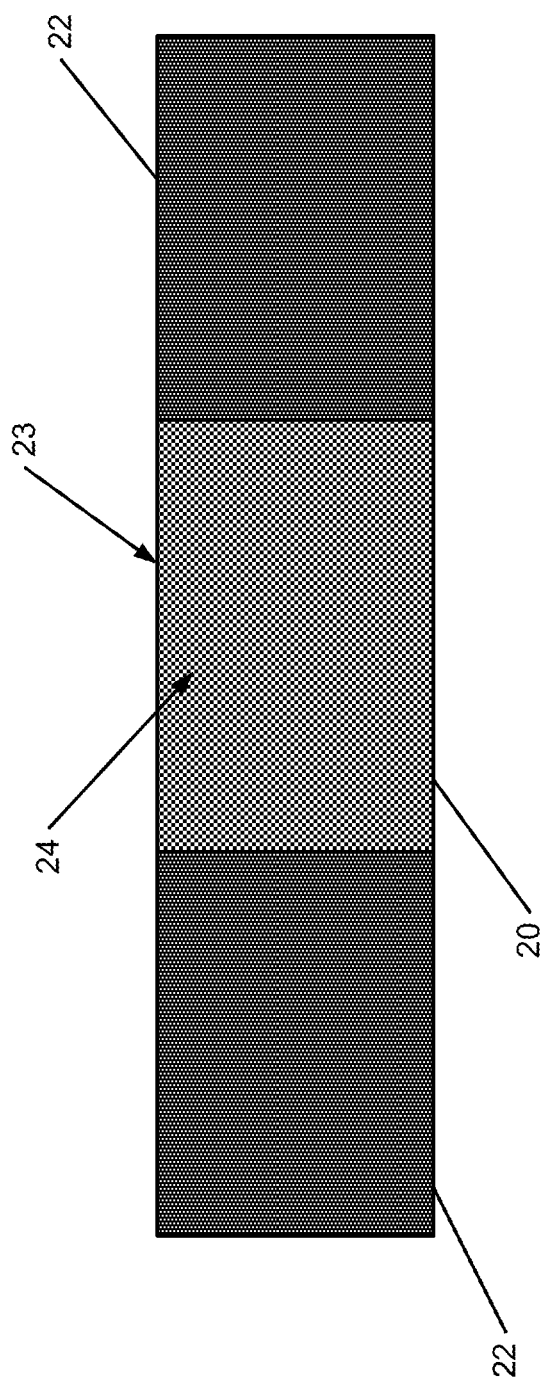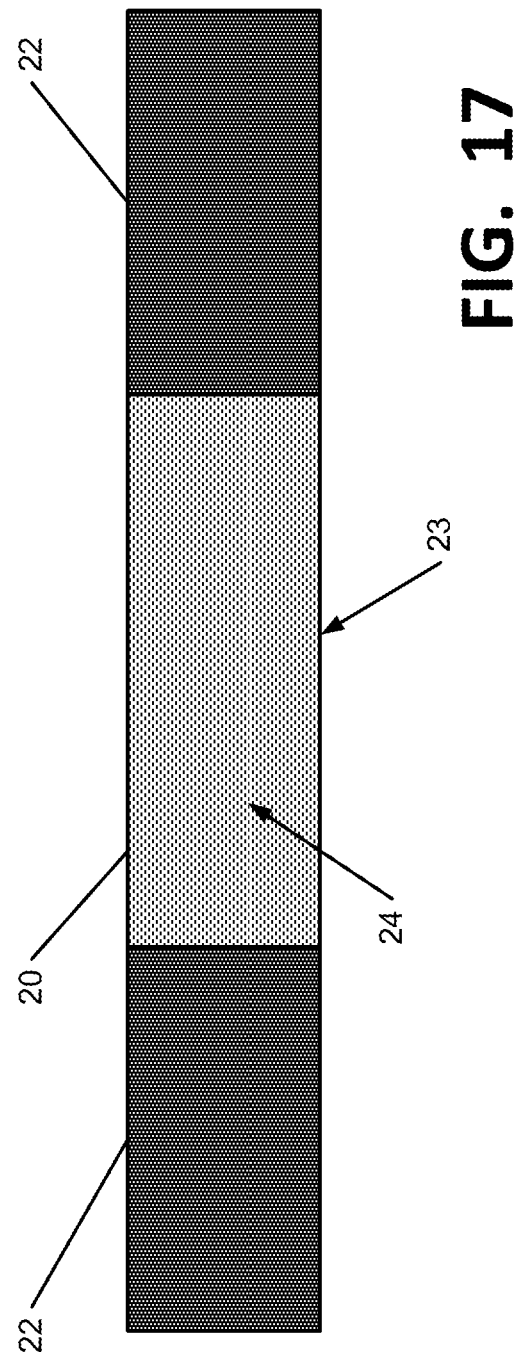

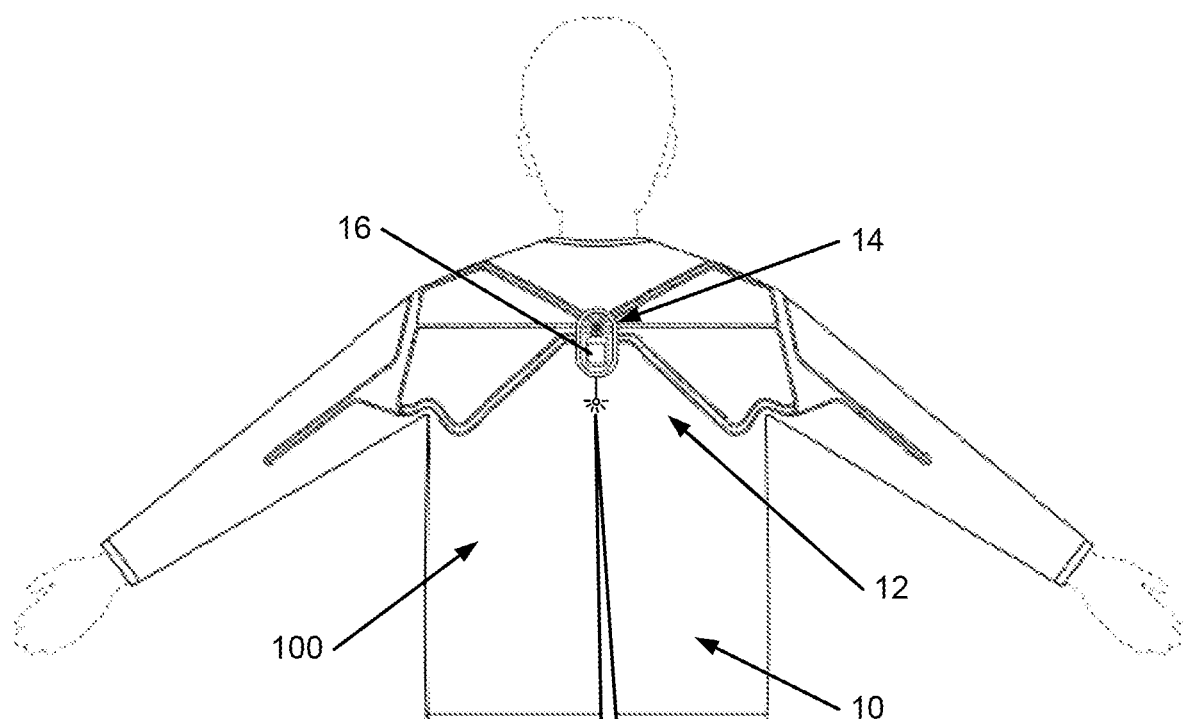
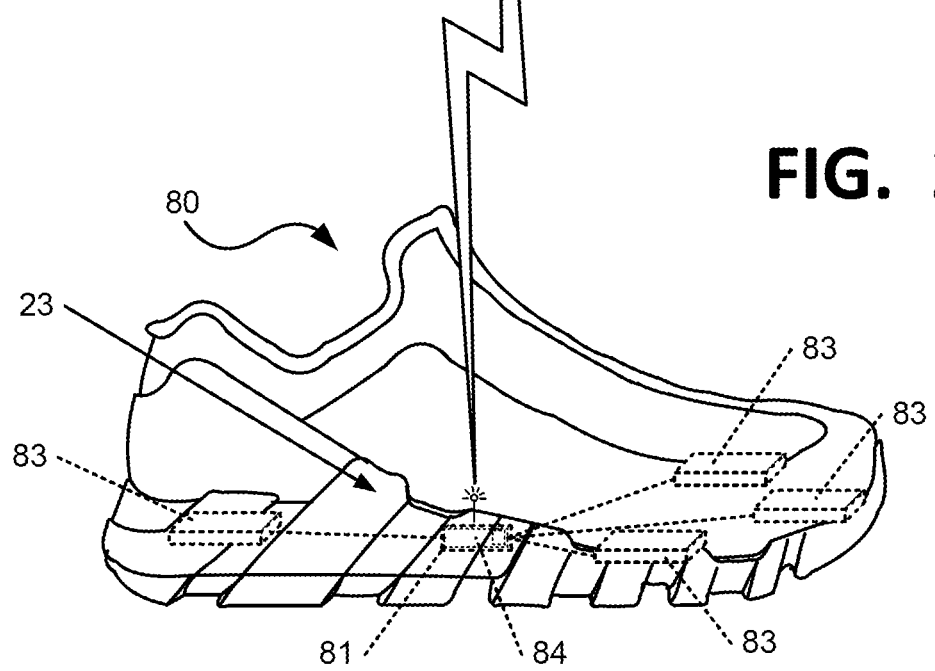
FIG. 20

APPAREL HAVING SENSOR SYSTEM

CROSS-REFERENCE TO RELATED APPLICATIONS

This application is a continuation of U.S. patent application Ser. No. 17/702,365, filed Mar. 23, 2022, which is a continuation of U.S. patent application Ser. No. 16/919,347, filed Jul. 2, 2020, and issued as U.S. Pat. No. 11,320,325 on May 3, 2022, which is a continuation of U.S. patent application Ser. No. 16/195,109, filed Nov. 19, 2018, and issued as U.S. Pat. No. 10,704,966 on Jul. 7, 2020, which is a continuation of U.S. patent application Ser. No. 15/824,593, filed Nov. 28, 2017, and issued as U.S. Pat. No. 10,139,293 on Nov. 27, 2018, which a continuation of U.S. patent application Ser. No. 14/702,299, filed May 1, 2015, and issued as U.S. Pat. No. 9,841,330 on Dec. 12, 2017, which is a continuation of U.S. patent application Ser. No. 13/713,967, filed Dec. 13, 2012, and issued as U.S. Pat. No. 9,043,004 on May 26, 2015, all of which prior applications are incorporated herein by reference.

TECHNICAL FIELD

The present invention generally relates to apparel having a sensor system and, more particularly, to an article of apparel having an extruded sensor system having a sensor member and a conductor connected to a communication port operably associated with the apparel.

BACKGROUND

Articles of apparel having sensor systems incorporated therein are known. Sensor systems track movement and collect performance data wherein the movements and performance data can be accessed for later use such as for analysis purposes. In certain systems, the sensor systems are complex or unreliable at times due to bending of the apparel at a wearer's joints. In addition, data can only be accessed or used with certain operating systems. Thus, uses for the collected data can be unnecessarily limited. Accordingly, while certain articles of apparel having sensor systems provide a number of advantageous features, they nevertheless have certain limitations. The present invention seeks to overcome certain of these limitations and other drawbacks of the prior art, and to provide new features not heretofore available.

BRIEF SUMMARY

The present invention relates generally to an article of apparel having a sensor system. Aspects of the invention relate to a sensor system that includes one or a plurality of sensors formed of a polymeric material having a conductive particulate material dispersed therein and conductive leads connected to the sensors. The leads may also be formed of a polymeric material having a conductive particulate material dispersed therein. The sensors and the leads may have the same or different polymeric materials and/or conductive particulate materials. In one embodiment, the conductive material is dispersed in the sensor(s) at a first dispersion density and the conductive material is dispersed in the leads at a second dispersion density that is higher than the first dispersion density. Each of the sensors is configured to increase in resistance when deformed under pressure, or in other words, the sensor has a first resistance in a non-deformed condition and a second resistance in a deformed condition, where the second resistance is higher than the first resistance. In a configuration where the leads include the dispersed conductive material, the second dispersion density is such that each of the leads has sufficient conductivity that the leads are configured to conduct an electronic signal between each sensor and the port in any state of deformation.

According to one aspect, the article of apparel further contains a communication port operably connected with the sensors, such that the leads connect the sensors to the port. In one embodiment, the communication port is configured for transmitting data regarding forces detected by each sensor in a universally readable format. The port may also be configured for connection to an electronic module to allow communication between the sensors and the module.

According to another aspect, the article of apparel contains an electronic module in communication with the sensors, which is configured for collecting data from the sensors. The module may be connected with the sensors through the communication port, and may be positioned within a cavity associated with the article of apparel. In one embodiment, the module is further configured for transmitting the data to an external device for further processing.

According to another aspect, the article of apparel may contain a housing that is configured for removably receiving the electronic module. The housing may include a well for receiving the module therein, and may have a communication port connected with the sensors and configured for communication with the module. The housing may further have retaining structure configured for retaining the module within the housing.

According to a further aspect, the polymeric material and the conductive particulate material of each sensor and each conductive lead are co-extruded.

According to an additional aspect, each lead includes an insulating coating disposed around a conductive core, with both the insulating coating and the conductive core being formed of the polymeric material. The insulating coating is substantially free of the conductive particulate material and the conductive core includes the conductive particulate material dispersed therein at the second dispersion density. Each sensor may additionally or alternately include an insulating coating disposed around a core, with both the insulating coating and the conductive core being formed of the polymeric material. The insulating coating is substantially free of the conductive particulate material and the core includes the conductive particulate material dispersed therein at the first dispersion density.

According to an additional aspect, at least one of the sensors includes a plurality of generally parallel branches having one or more bridges extending transverse to the branches to connect the branches together. Such sensor(s) may have three or more branches arranged in a zigzag pattern.

According to an additional aspect, the sensors may be formed by a first polymeric paint having the conductive particulate material dispersed therein at the first dispersion density, and the leads may be formed by a second polymeric paint having the conductive particulate material dispersed therein at the second dispersion density. The first polymeric paint and the second polymeric paint both may be silicone-based paints.

According to an additional aspect, the conductive particulate material includes at least one particulate material selected from a group consisting of: nickel, silver, carbon, and aluminum.

According to an additional aspect, at least one of the sensors includes a thinned segment having a width that is reduced relative to other portions of the sensor.

According to an additional aspect, each sensor has two leads connecting the sensor to the port, and each sensor and the two leads connected thereto are integrally formed as a single extruded member having a sensor segment forming the sensor and conductor segments forming the leads. The sensor segment may be formed of the polymeric material having the conductive particulate material dispersed therein at the first dispersion density, and the conductor segments may be formed of the polymeric material having the conductive particulate material dispersed therein at the second dispersion density.

Additional aspects of the invention relate to an article of apparel that includes a sensor system as described above. The article of apparel may be a shirt, which may have sensors located at least in elbow regions, shoulder regions, and/or underarm regions of the shirt, and which may have the port located in the upper back region or the chest region. The article of apparel may be a pair of pants (including shorts), which may have sensors located at least in knee regions and the back region of the pants, and which may have the port located on the front or back region of the waist region of the pants. The article of apparel may further be a full bodysuit, having one or more sensors and a port located in one of the locations described above with respect to the shirt and pants. The article of apparel may further be a tracksuit or similar outfit having separate shirt and pants members. The sensor systems of the shirt and pants may share a single port, or may have separate ports that may communicate with each other and/or with a common external device. Other articles of apparel may be utilized as well.

Additional aspects of the invention relate to an article of apparel that includes a clothing member having a sensor system disposed thereon. The sensor system includes an extruded silicone member having a sensor segment and a conductor segment connected to the sensor segment and continuous with the sensor segment. The sensor segment has a conductive particulate material contained therein at a first concentration and the conductor segment having the conductive particulate material contained therein at a second concentration, the second concentration being greater than the first concentration. The sensor segments and conductor segments may form one or more sensors and leads, respectively, as described above.

Further aspects of the invention relate to a system that includes an article of apparel and/or a sensor system as described above, with an electronic module connected to the sensor system. The system may further have an external device configured for communication with the electronic module. The module is configured to receive data from the sensors and to transmit the data to the external device, and the external device is configured for further processing the data.

According to one aspect, the system also includes an accessory device connected to the external device, configured to enable communication between the electronic module and the external device. The accessory device may also be configured for connection to a second external device to enable communication between the electronic module and the second external device.

According to another aspect, the data communicated to the external device can be used in one or more different applications. Such applications can include using the data as control input for a program executed by the external device, such as a game program, or for athletic performance monitoring, among other applications. Athletic performance monitoring can include monitoring one or more performance metrics such as speed, distance, lateral movement, acceleration, jump height, weight transfer, foot strike pattern, balance, foot pronation or supination, loft time measurement during running, lateral cutting force, contact time, center of pressure, throwing arm speed/force, kicking leg speed/force, weight distribution, and/or impact force, among others.

Still further aspects of the invention relate to methods utilizing an article of apparel containing a sensor system as described above. Such methods can include receiving data from the sensors at the electronic module and transmitting the data from the module to a remote external device for further processing, which may include use in one or more applications. Such methods can also include removing or disconnecting a first electronic module from the sensor system and connecting a second module in its place, where the second module is configured for a different operation. Such methods can further include processing the data for use in one or more applications and/or using the data as control input for an external device. Still further, such methods can include an external device receiving the data and utilizing and/or further processing the data in a variety of manners, including as control input, for athletic monitoring or modeling, and other such uses. Aspects of the invention may also include computer-readable media containing instructions for use in performing one or more features of these methods and/or utilizing the footwear and systems described above.

Other aspects of the invention relate to a system that includes at least one article of apparel having a sensor system as described above, as well as at least one article of footwear having a sensor system that includes one or more sensors in communication with a port. Electronic modules can be connected to the sensor systems, and each electronic module is configured for communicating data received from the sensors to an external device. The data from the different sensor systems may be integrated and processed together, such as by the modules and/or the external device, and may be used in any of the applications described above. The system may use one of several different communication modes.

Still other features and advantages of the invention will be apparent from the following specification taken in conjunction with the following drawings.

BRIEF DESCRIPTION OF THE DRAWINGS

FIG. 3 is a cross-sectional view of a portion of a housing of the shirt of FIG. 2;

FIG. 16 is a schematic cross-sectional view of a sensor of one embodiment of a sensor system according to aspects of the present invention, with leads connected to the sensor;

FIG. 17 is a schematic cross-sectional view of the sensor of FIG. 16 in a state of tensile deformation;

FIG. 20 is a perspective view of an article of footwear including a sensor system in communication with the sensor system of the article of FIG. 1, according to aspects of the present invention.

DETAILED DESCRIPTION

Figure 1:
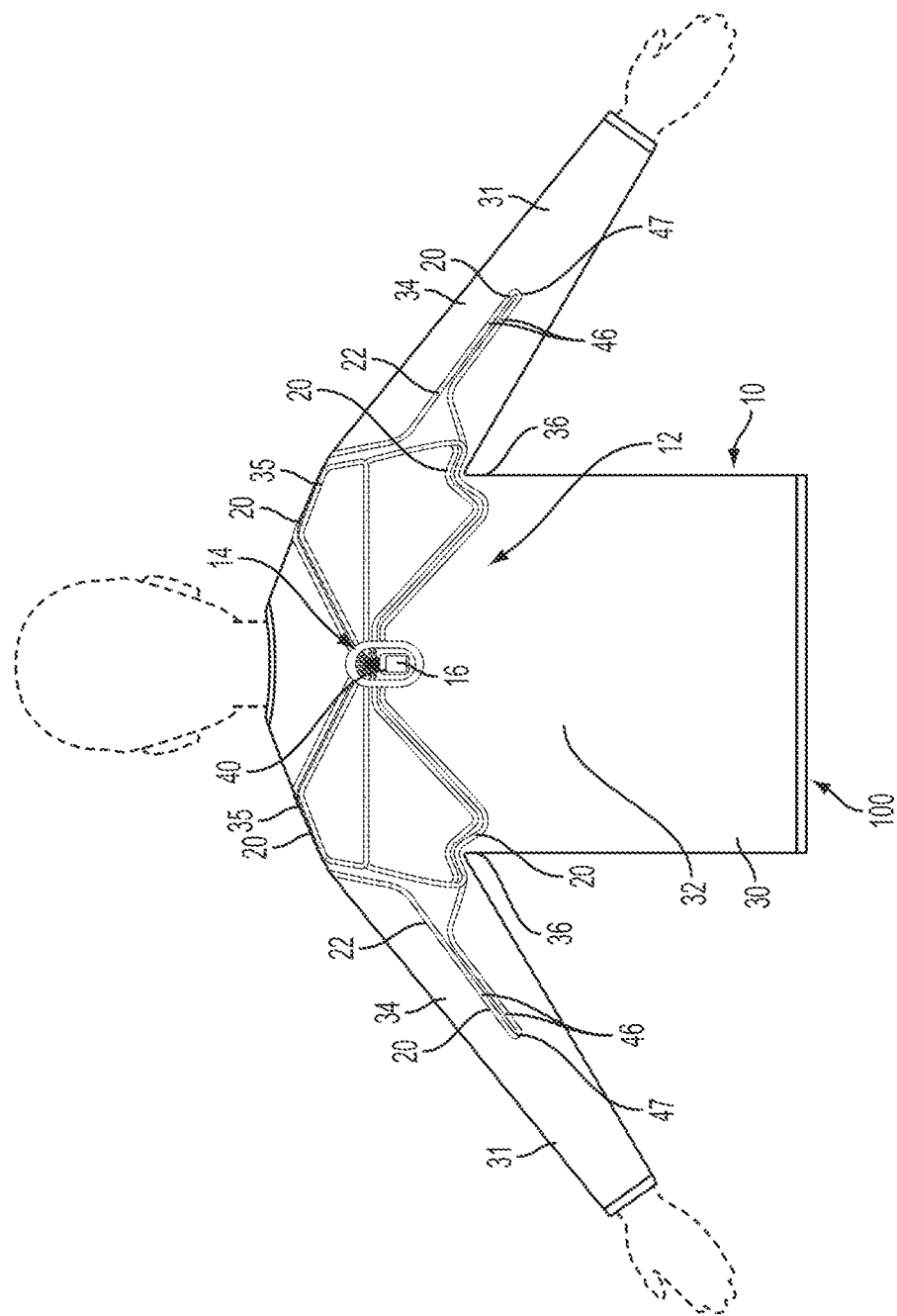
FIG. 1 is a rear view of one embodiment of an article of apparel in the form of a shirt having a sensor system.

While this invention is susceptible of embodiment in many different forms, there are shown in the drawings, and will herein be described in detail, preferred embodiments of the invention with the understanding that the present disclosure is to be considered as an exemplification of the principles of the invention and is not intended to limit the broad aspects of the invention to the embodiments illustrated and described.

Figure 11:
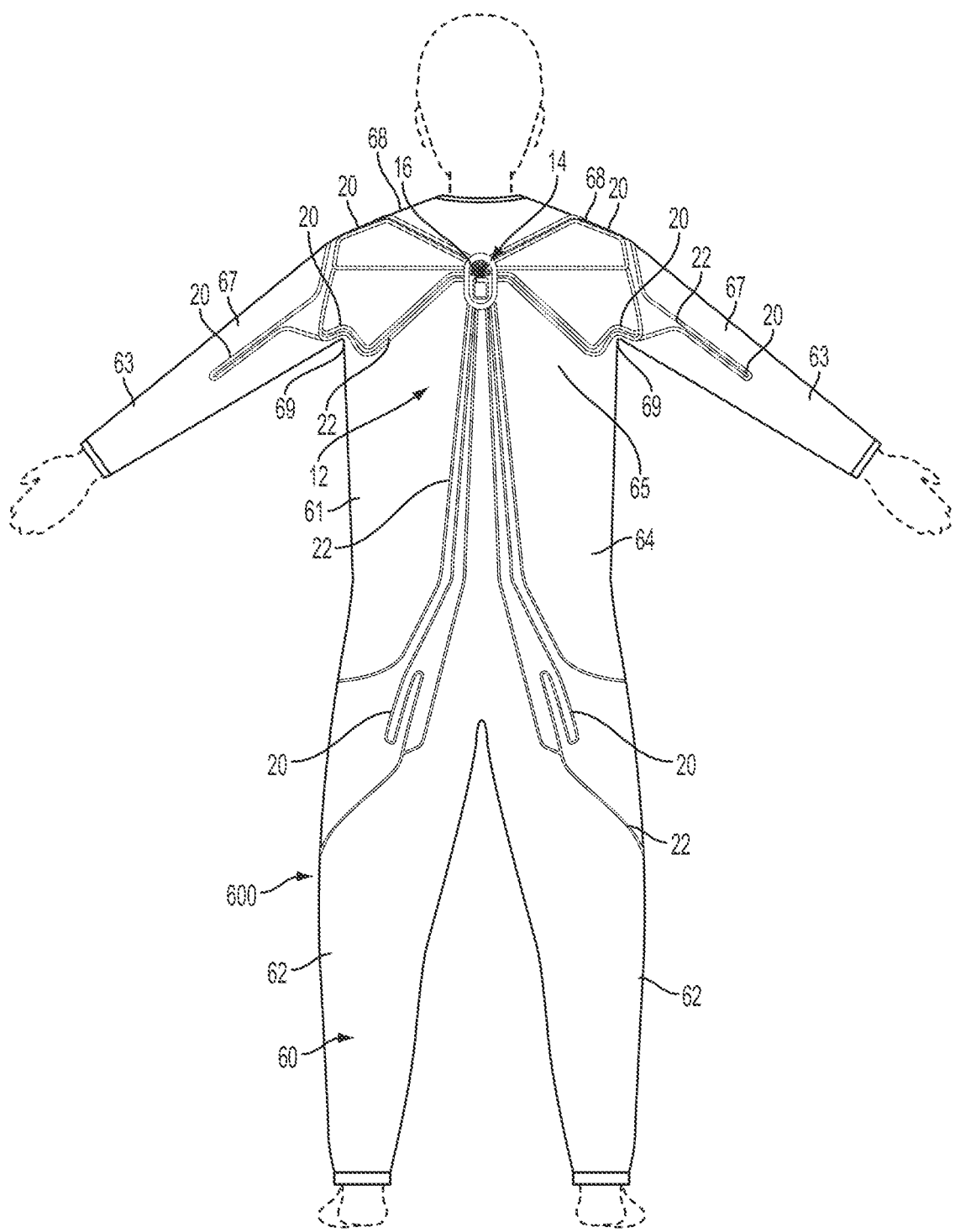
FIG. 11 is a rear view of another embodiment of an article of apparel in the form of a bodysuit having a sensor system.
Figure 12:
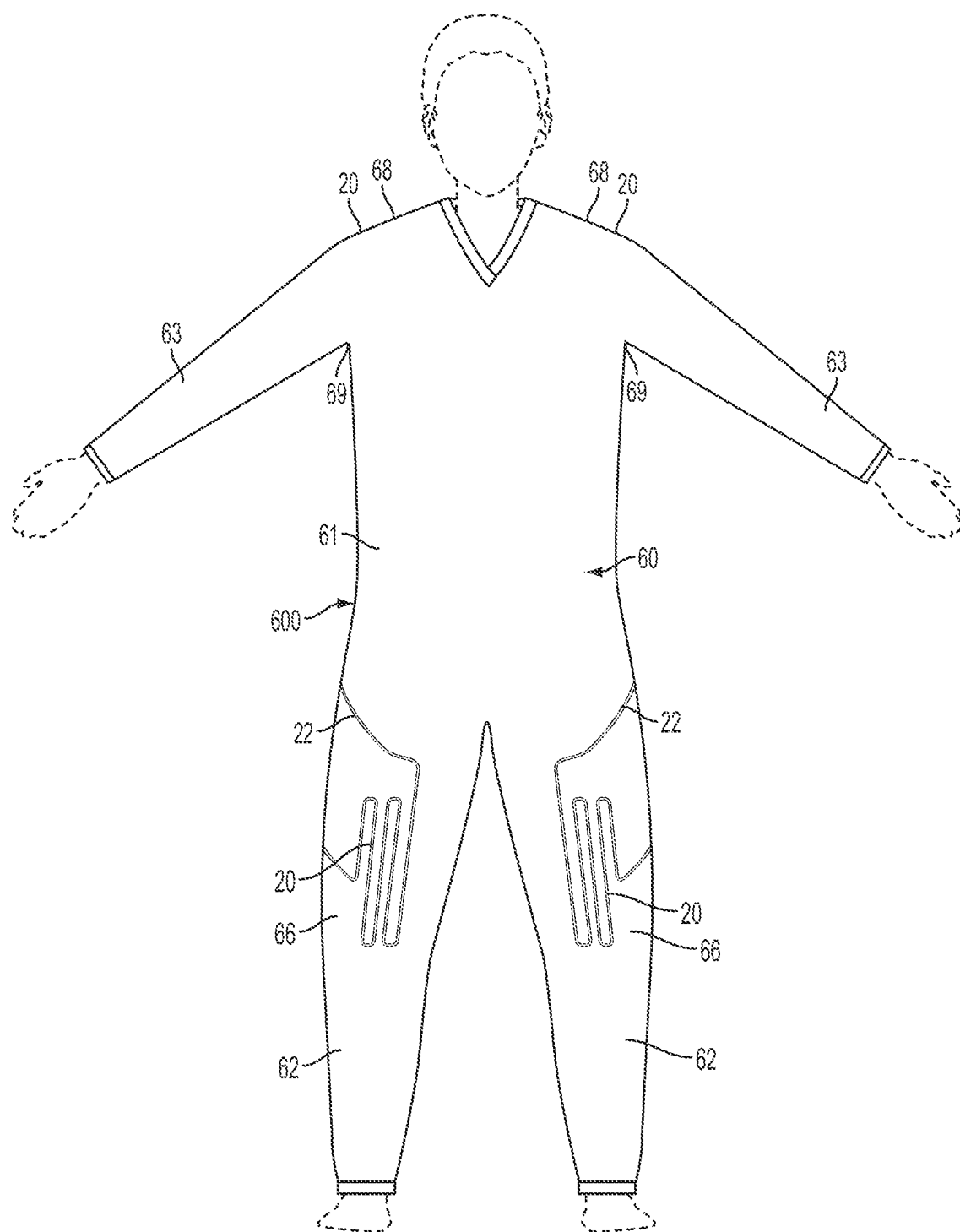
FIG. 12 is a front view of the bodysuit of FIG. 11.

Aspects of the present invention may be used in connection with an article of apparel 100 that includes a clothing member, for example, an clothing member 10 in the form of a shirt, as shown in FIGS. 1-6, a pair of pants 50, as shown in FIGS. 7-10, a bodysuit 60 as shown in FIGS. 11-12, or other article of apparel, such as gloves, footwear (including socks, shoes, etc.), other types of shirts (including short sleeve or sleeveless shirts), other types of pants (including shorts), hats or other headgear, coats or other outerwear, arm or leg bands, belts, or any other type of apparel that is configured to cover and/or be worn on any part of a user's body. In general, the article of apparel has a sensor system 12 connected thereto and/or disposed thereon, which includes a port 14 adapted for connection to an electronic module 16 or other device, one or more sensors 20, and one or more sensor leads 22 connecting the sensors 20 to the port 14.

The clothing member 10 is configured as a shirt to be worn on a user's upper body, and as illustrated in FIG. 1, includes a trunk portion 30 with sleeves 31 extending from the sides of the trunk portion 30 and configured to at least partially cover the user's arms. The trunk portion 30 has a back region 32 configured to at least partially cover the user's back, a chest region 33 configured to at least partially cover the user's chest. The sleeves 31 have elbow regions 34 configured to at least partially cover the user's elbows. Shoulder regions 35 and underarm regions 36 connect the sleeves 31 to the trunk portion 30 and are configured to at least partially cover the user's shoulders and underarms, respectively. While the port 14 may be located in a variety of positions without departing from the invention, in one embodiment, the port 14 is provided at a position and orientation and/or is otherwise structured so as to avoid or minimize contact with and/or irritation of the user's body, such as during an athletic activity. The positioning of the port 14 in FIGS. 1-6 illustrates one such example. In this embodiment, the port 14 is located in the upper part of the back region 32 of the clothing member 10, but may be located elsewhere in other embodiments, for example, the chest region 33, other areas of the trunk portion 30, or on one of the sleeves 31. The port 14 and/or the clothing member 10 may include additional structure to increase comfort for the user.

One example embodiment of the sensor system 12 is illustrated in FIGS. 1-6. In general, the sensor system 12 includes one or more sensors 20 that are connected to the clothing member 10. The sensors 20 are formed of a flexible, insulative matrix material with a conductive particulate material dispersed therein. The flexible material may be an insulative polymer material, such as silicone in one embodiment, and may alternately be another polymeric material such as polyurethane, or other flexible material. The conductive particulate material may be a metallic material, such as nickel, silver, gold, copper, aluminum, or other conductive metallic material (including alloys thereof), as well as carbon or other conductive material, and may further include a combination of conductive materials. The conductive particulate material may be in any particulate form, including powder, flakes, needles, etc., or a combination of such forms. FIGS. 16-17 illustrate example embodiments of a sensor 20, showing the flexible polymer matrix material 23 with the conductive material 24 dispersed within the polymer material 23.

The sensors 20 have a conductivity (and resistivity) that varies based on deformation and applied force, and may be considered to be a force-sensitive resistive material. The mechanism by which this occurs is that the deformation of the matrix material 23 causes the distance between the particles of the conductive material 24 to increase or decrease, which changes the resistance or conductivity of the material. For example, as shown in FIG. 17, when the matrix material 23 is stretched (e.g. tensile deformation), the distance between the particles of the conductive material 24 increases, which increases the resistance and decreases the conductivity of the sensor 20 relative to the sensor 20 as shown in FIG. 16. The concentration or dispersion density of the conductive material in the sensors 20 may be such that the change in resistance due to typical deformation of the sensor 20 is significant enough to be accurately measurable. This density may be dependent on the identity of the conductive material 24 and/or the matrix material 23.

In one embodiment, the sensors 20 may have multiple connected branches 46 that extend across a common pressure point (e.g. a flex point as described below). As shown in FIG. 1, at the elbow regions 34, the branches 46 may be oriented parallel or generally parallel to each other, and may be arranged in an alternating or "zig-zag" configuration in one embodiment, having one or more bridges 47 extending transversely between the branches to connect adjacent branches 46 together. Other configurations and orientations may be utilize in other embodiments. In this configuration, all of the multiple branches 46 share a single pair of leads 22 and operate as a single sensor 20. If any of the branches 46 is sufficiently deformed the module 16 will register deformation by the sensor. As a result, the detection of the sensors 20 can be more consistent, as different movements may deform different branches 46 of the sensor 20. Additionally, the sensors 20 may be positioned differently with respect to the user's joints due to the user wearing the clothing member 10 in a slightly different configuration, slippage of the clothing member 10 during use, differences in size/anatomy between different people, etc. The multiple branches 46 of the sensors 20 allow for detection of movement in any of these situations. Further, this consistency permits the article 100 to be sold commercially in a single configuration that is effective for a large number of users, avoiding the need for costly customization.

The sensors 20 may also contain one or more thinned portions or segments that have a width that is smaller than the widths of other portions of the sensors 20 and/or the widths of the leads 22. The reduced thickness of the thinned segments ensures that the sensor 20 is deformed across its entire width, in order to produce consistent resistivity change across the width of the sensor 20 and thereby produce greater consistency in detection of movement. In another embodiment, the entire sensor 20 may have reduced width for this purpose, including a width that is reduced with respect to the widths of the leads 22.

The sensor system 12 also includes sensor leads 22 connecting the sensors 20 to the port 14. In the embodiment illustrated in FIGS. 1-6, the leads 22 are also formed of a flexible, insulative matrix material 25 with a conductive particulate material 26 dispersed therein. Any materials listed above with respect to the sensors 20 may be used for the leads 22 as well. In one embodiment, the matrix material 23 and the conductive material 24 of the sensors 20 are the same as the materials 25, 26 of the leads 22. In another embodiment, one or both of the conductive material 26 and the matrix material 25 of the leads 22 may be different from the materials 23, 24 of the sensors 20. It is understood that the sensor system 12 may include a combination of different sensors 20 and/or leads 22 that include different matrix and/or conductive materials, which can be used to achieve different functionalities. The leads 22 may be formed of a different configuration in another embodiment, such as a conductive wire with an insulating coating or a thread with a conductive plating (e.g. silver). Such wires or threads could be woven into the fabric of the clothing member 10 in one embodiment.

In general, the leads 22 have greater conductivity than the sensors 20, and have sufficient conductivity to conduct an electronic signal between the sensor 20 and the port 14 in substantially any state of deformation (excluding extreme deformation, such as fracture). In the embodiment of FIGS. 1-6, the concentration or dispersion density of the conductive material 26 in the leads 22 is greater than the dispersion density in the sensors 20, as shown in FIGS. 16-17, to create the increased conductivity. The dispersion density of the conductive material 26 in the leads 22 may be such that normal or typical deformation of the leads 22 does not cause a significant or measurable decrease in conductivity. This density may be dependent on the identity of the conductive material 26 and/or the matrix material 25.

In one embodiment, as shown in FIG. 1, each sensor 20 has two leads 22 connecting the sensor 20 to the port 14, one of which serves as a power lead and one of which serves as a return or ground. In another embodiment, the sensor system may include a single ground lead 22 (or alternately, a single power lead) connected to a plurality of different sensors 20, with the sensors 20 having separate power leads 22 (or alternately, separate ground leads). In a further embodiment, two or more of the sensors 20 may share a pair of leads 22, and may be arranged in a single "loop" with a pair of leads connecting the sensors 20 to the port 14. These sensors 20 may be considered to be a "set" of sensors 20. For example, in one embodiment, each of the branches 46 in the alternating sensor 20 configuration as shown in FIG. 1 may be configured as separate sensors 20, with the bridges 47 in the form of auxiliary leads having higher conductivity connecting the separate sensors 20, such that the sensors 20 share a pair of main leads 22 and are arranged in a set. In this configuration, the sensors 20 of the set would be arranged in series, but in another embodiment, two or more sensors 20 may be arranged in parallel. Further configurations of sensors 20 and leads 22 are contemplated.

In one embodiment, the sensors 20 and the leads 22 may be formed and connected to the clothing member 10 by applying as a paint or similar substance that can be applied in a flowable form which then solidifies (such as through drying, curing, etc.). The sensors 20 and the leads 22 can be applied as different types of paints, such as a first paint with the conductive material at lower dispersion density to form the sensors 20 and a second paint with the conductive material at a higher dispersion density to form the leads 22. A primer, adhesive, or other bonding material may be used to enhance the connection between the paint and the clothing member in one embodiment. Additionally, the use of paint or a similar technique to apply the sensors 20 and leads 22 may facilitate customization of the article 100 for a particular user, enabling the sensors 20 and leads 22 to be quickly formed in a desired pattern or configuration.

In another embodiment, the sensors 20 and the leads 22 may be formed by extrusion. The sensor matrix material 23 may be doped with the sensor conductive material 24 at the appropriate distribution density, loaded into an extrusion device, and extruded to form the sensors 20. Similarly, the lead matrix material 25 may be doped with the lead conductive material 26 at the appropriate distribution density, loaded into an extrusion device, and extruded to form the leads 22. The extruded sensors 20 and leads 22 may be connected to the clothing member 10 by extruding the sensors 20 and the leads 22 directly onto the clothing member 10 in a desired pattern, in one embodiment. As similarly mentioned above, a primer, adhesive, or other bonding material may be used to enhance the connection between the extruded material and the clothing member in one embodiment. Other forming methods may be used in other embodiments.

In one embodiment, the sensors 20 and the leads 22 can be formed together in one embodiment as a continuous member formed of the matrix material 23, 25, with different segments having different concentrations of the conductive material to form the sensors 20 and leads 22. Co-extrusion, other extrusion techniques, or another effective method may be utilized to produce the continuous member. In one example embodiment, as shown in FIG. 1, each sensor 20 or set of sensors 20 and the lead or leads 22 connecting the sensor(s) 20 to the port 14 may be a single continuous member formed of a single matrix material (e.g. silicone), having one or more sensor segments 27 and one or more conductor segments 28 that are continuous with each other. The sensor segments 27 have the conductive material 24 dispersed therein at the appropriate concentration to form the sensors 20, and the conductor segments 28 have the conductive material 26 dispersed therein at the appropriate concentration to form the leads 22. It is understood that in this embodiment, the conductive materials 24, 26 of the sensors 20 and the leads 22 may be the same or different materials. In another embodiment, different matrix materials 23, 25 may be used for the sensor segments 27 and the conductor segments 28, if such materials 23, 25 can be sufficiently bonded to form the single continuous member.

Figure 18:
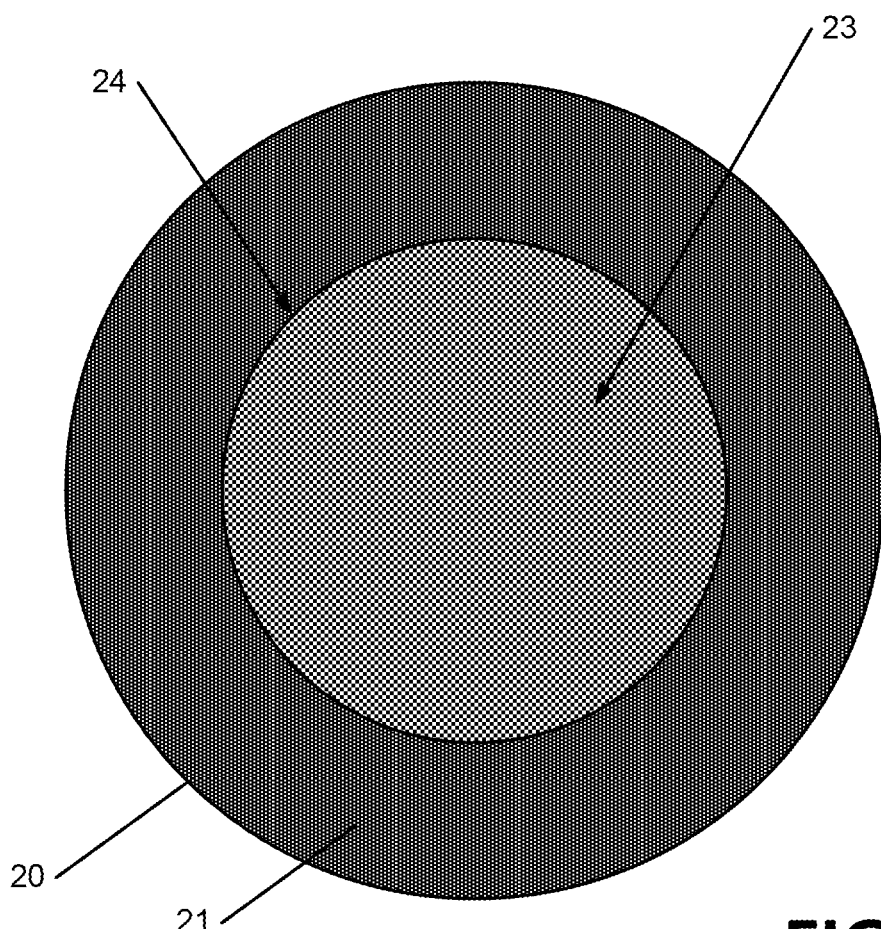
FIG. 18 is a schematic cross-sectional view of a sensor of another embodiment of a sensor system according to aspects of the present invention.
Figure 19:
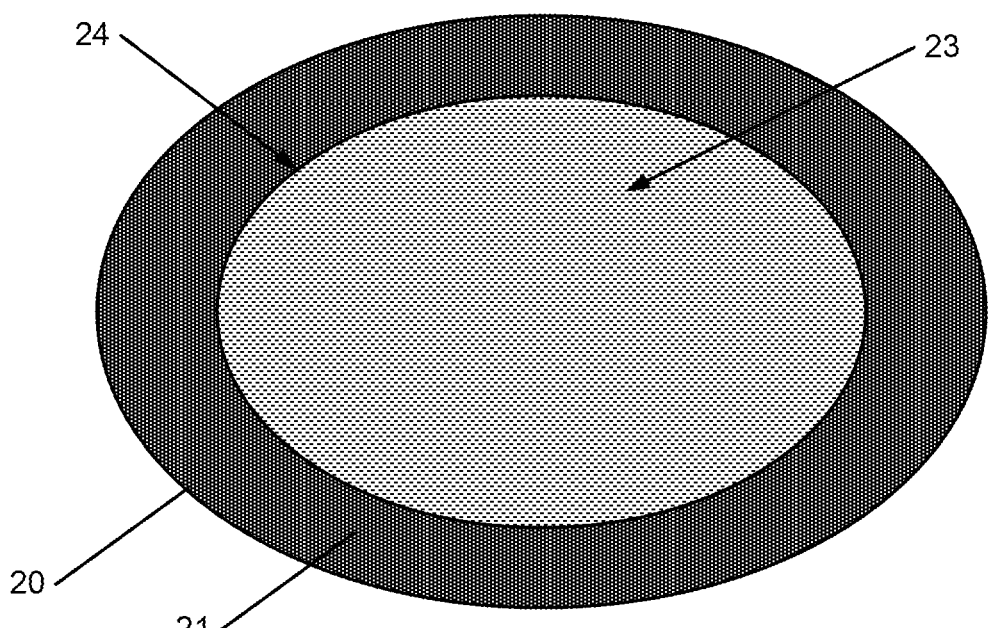
FIG. 19 is a schematic cross-sectional view of the sensor of FIG. 18 in a state of tensile deformation.

In another embodiment, sensors 20 and/or leads 22 as described above may have an insulative coating 21, such as illustrated in FIGS. 18-19. The insulative coating 21 may be formed of the same material as the matrix material(s) 23, 25 of the sensors 20 and/or leads 22 in one embodiment, and may further be co-extruded along with the sensors 20 and/or leads 22 or otherwise continuously and integrally formed with the sensors 20 and/or leads 22 in an additional embodiment. Alternately, the insulative coating 21 may be made from one or more different materials, or may be made from the same material as the matrix material(s) 23, 25 while being separately formed. FIG. 19 illustrates tensile deformation of the sensor 20, which increases the resistivity of the sensor 20 according to the same mechanism described above.

FIGS. 1-6 illustrate one example embodiment of the article 100, showing the positioning of the sensors 20. The sensors 20 may be positioned at or near flex points on the article 100, which are configured to be positioned on portions of the user's body where movement is focused (e.g. joints). As seen in FIG. 1, sensors 20 are positioned on each of the elbow regions 34, with leads 22 that extend from the sensors 20 to the port 14 located in the back region 32 of the clothing member 10. These sensors 20 deform when the user's elbows are bent. Additional sensors 20 are positioned on the back sides of each of the shoulder regions 35 and in each underarm region 36 of the clothing member 10, with leads 22 connecting each sensor 20 to the port 14. These sensors 20 deform when the user's arms are raised and lowered or moved forward and backward. As described above, the deformation of these sensors 20 causes the resistance of the sensors 20 to change, which is detected by the module 16 through communication through the leads 22 and the port 14. As shown, all the sensors 20 and the leads 22 are connected to the outer surface of the clothing member 10. In another embodiment, at least some of the sensors 20 and/or leads 22 may be connected to the inner surface of the clothing member 10 or embedded within the clothing member 10, or a combination of such configurations. It is understood that the article 100 may include additional sensors 20 and/or sensors 20 in other positions in other embodiments.

The port 14 is configured for connection to the leads 22 using a plurality of connectors or connection pins 13, which may be or include metallic (e.g. silver) threads or other conductors. The port 14 also includes an interface 18 configured for communication with an interface 17 of the module 16. Each of the interfaces 17, 18 may include a plurality of electrical contacts (not shown) or other connections. In one embodiment, the interfaces 17, 18 include separate electrical contacts corresponding to each of the leads 22. A harness member 11 supports the connection pins 13 in connection with the leads 22 and consolidates the pins 13 together to connect to the interface 18. The harness member 11 may be made from a sheet-like polymer material, with the pins 13 at least partially embedded therein. A frame member 19 may be positioned around the harness member 11, to support the harness member 11, provide a point for connection to the clothing member 10, and cover the connections between the leads 22 and the pins 13, among other functions. The frame member 19 may be formed of a polymer foam or other suitable material.

Figure 2:
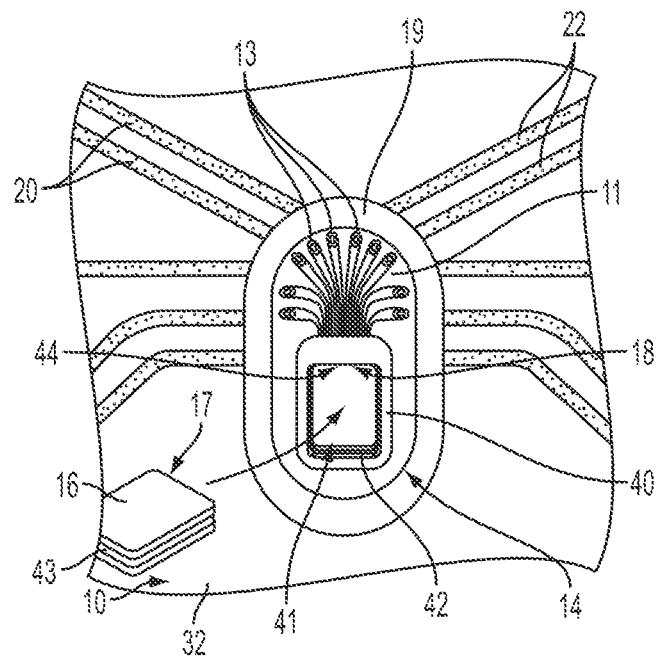
FIG. 2 is a magnified view of a portion of the shirt of FIG. 1.
Figure 4:
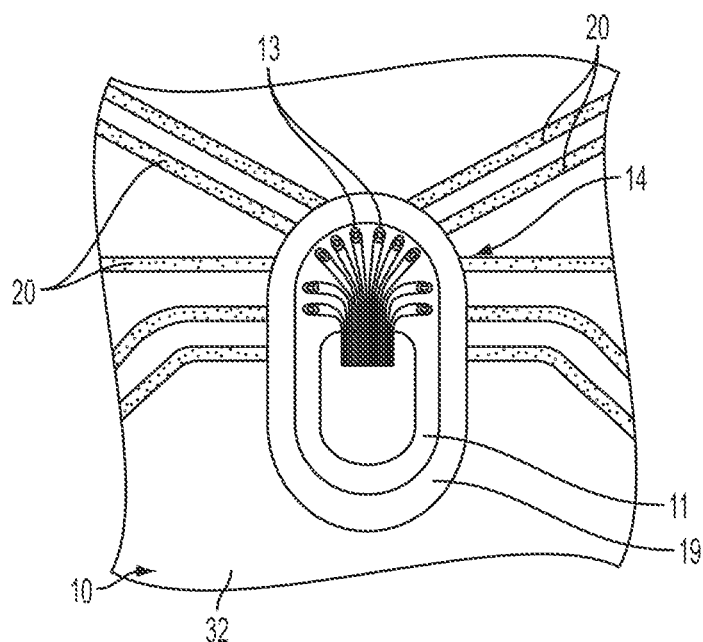
FIG. 4 is a magnified view as shown in FIG. 2, having the housing removed to show detail.
Figure 5:
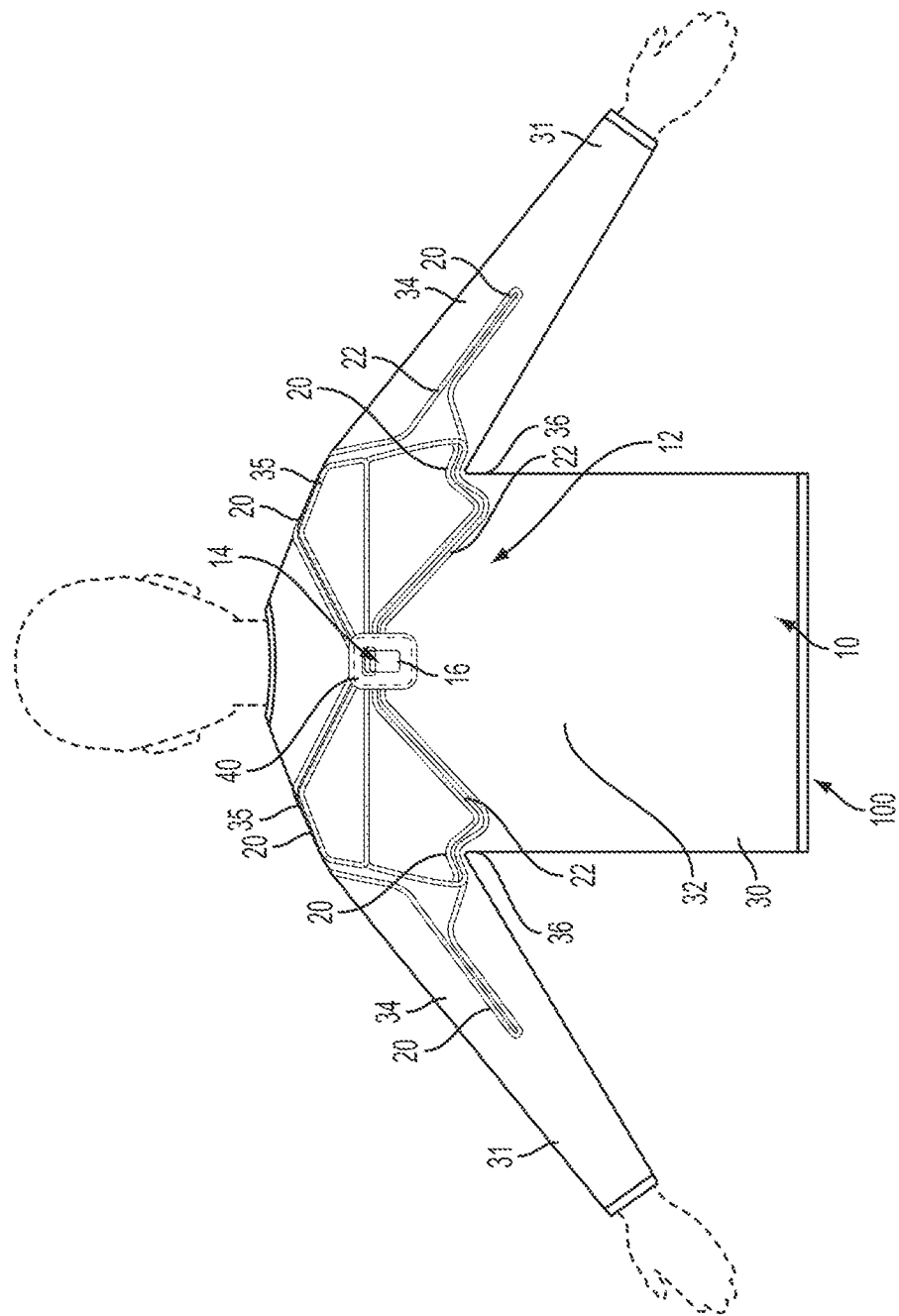
FIG. 5 is a rear view as shown in FIG. 1, with an alternate housing attached to the shirt.
Figure 6:
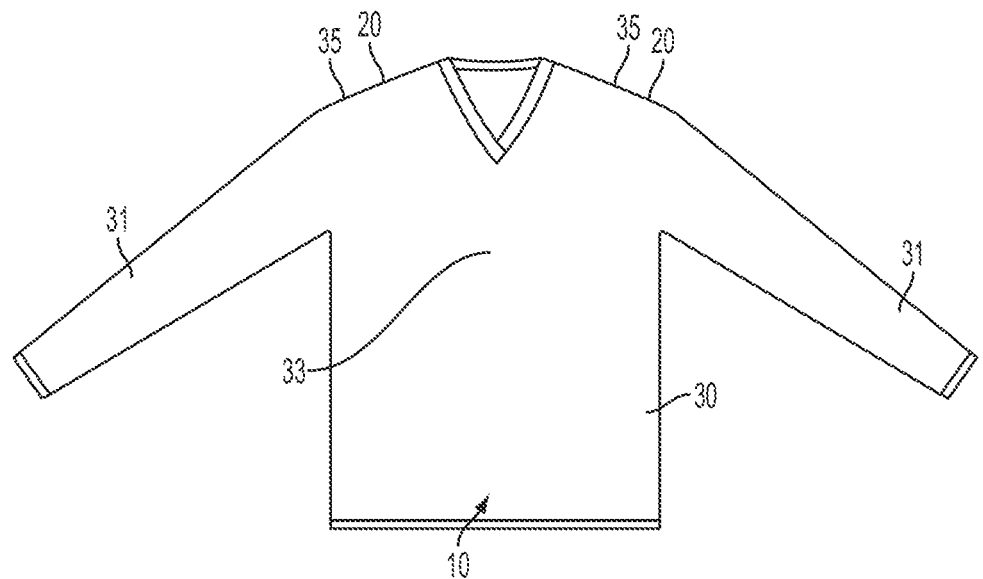
FIG. 6 is a front view of the shirt of FIG. 1.

In the embodiment illustrated in FIGS. 1-6, a housing 40 is connected to the clothing member 10 adjacent the port 14, and is positioned and configured to hold the module 16 in connection with the port 14. In one embodiment, as illustrated in FIGS. 1-3, the housing 40 is formed of a rigid shell, such as a rigid polymeric or metallic shell, that defines a well 41. In this embodiment, the housing 40 is formed of inner and outer members 45A, 45B that fit together by snapping, interference fit, or other mechanical connection, and are connected to the clothing member 10 by clamping a portion of the clothing member 10 between the inner and outer members 45A, 45B, as illustrated in FIG. 3. In the embodiment shown in FIG. 3, the inner member 45A includes a bottom wall supporting the module 16, however in another embodiment, the housing 40 may include an inner member 45A that is annular or partially annular and connects to the outer member 45B around the outer edges, with a center space allowing the portion of the clothing member 10 to form the bottom wall of the housing 40. In another embodiment, the housing 40 may be formed of leather or similar material (including synthetics) and is connected to the clothing member 10 by stitching around the periphery, as illustrated in FIG. 5. The housing 40 may alternately be formed of another material with some degree of structural stability, such as a metallic material or a polymeric material (including polymer-matrix composites). Additionally, the housing 40 may be connected to the clothing member 10 in another manner, including adhesives or other bonding materials, mechanical fastening, etc. In other embodiments, the housing 40 may have a different shape, size, structure, or positioning on the clothing member 10, or the port 14 may not have a housing associated with it, such as if the port 14 is configured to use a wireless interface.

The housing 40 may have a well 41 that is configured to receive at least a portion of the module 16 therein, and may further include a retaining structure to retain the module 16. This retaining structure may be complementary with retaining structure on the module 16. For example, in the embodiment shown in FIGS. 1-2 and the embodiment of FIG. 5, the housing 40 has retaining structure in the form of a flange 42 around the well 41, and the module 16 has a peripheral groove 43 that receives the flange 42 to retain the module 16 in the housing. The housing 40 in FIGS. 3 and 5 further includes a receiver 44 at one end of the well 41 that receives the end of the module 16 that includes the module interface 17 and acts as further retaining structure for the module 16. The port interface 18 is at least partially exposed within the receiver 44, such that when the module 16 is received in the receiver 44, the interfaces 17, 18 are in contact with each other to enable communication between the port 14 and the module 16. In other embodiments, the housing 40 and/or the module 16 may include different types of retaining structures, including retaining tabs or other releasable retaining structures. For example, the port 14 and/or the module 16 may include interfaces 17, 18 and/or retaining structure that is similar to the embodiments described and shown in U.S. patent application Ser. No. 11/416,458, published as U.S. Patent Application Publication No. 2007/0260421; U.S. patent application Ser. No. 13/401,918; U.S. patent application Ser. No. 12/483,824, published as U.S. Patent Application Publication No. 2010/0063778; U.S. patent application Ser. No. 12/483,828, published as U.S. Patent Application Publication No. 2010/0063779; and U.S. patent application Ser. Nos. 13/399,778 and 13/399,935, all of which applications are incorporated by reference herein in their entireties and made part hereof.

Figure 7:
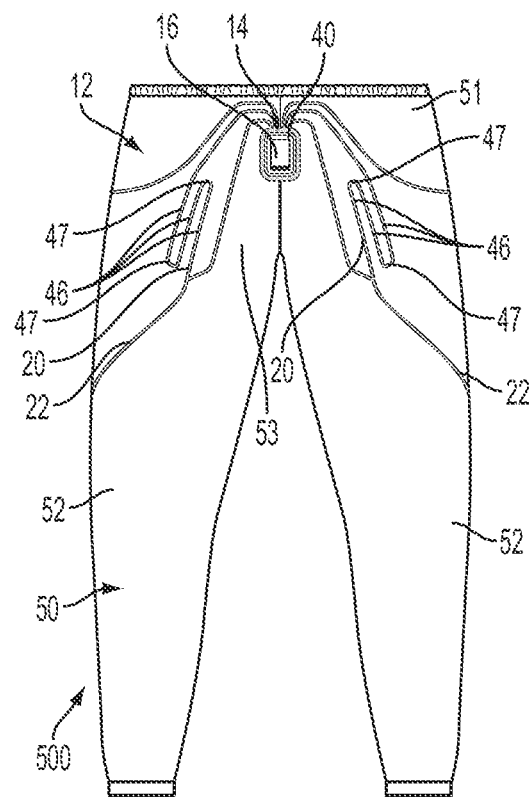
FIG. 7 is a rear view of another embodiment of an article of apparel in the form of pants having a sensor system.
Figure 8:
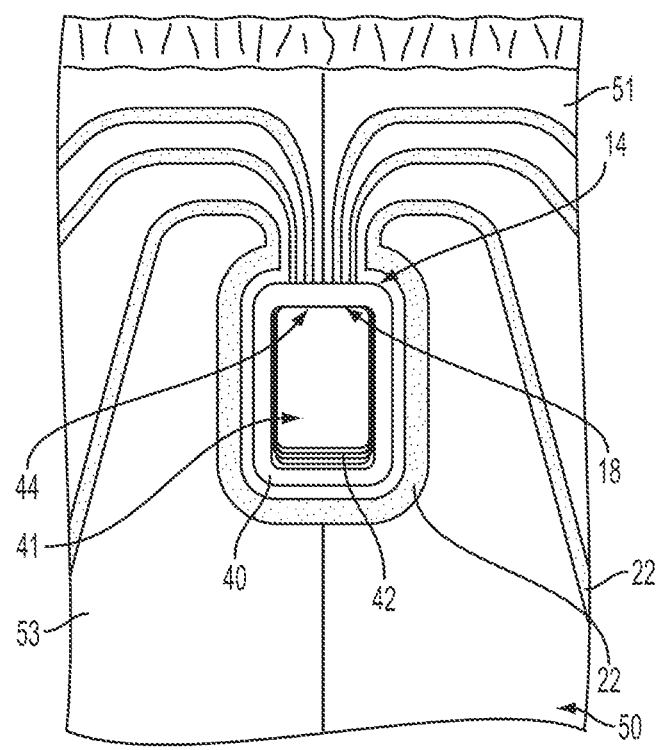
FIG. 8 is a magnified view of a portion of the pants of FIG. 7.
Figure 9:
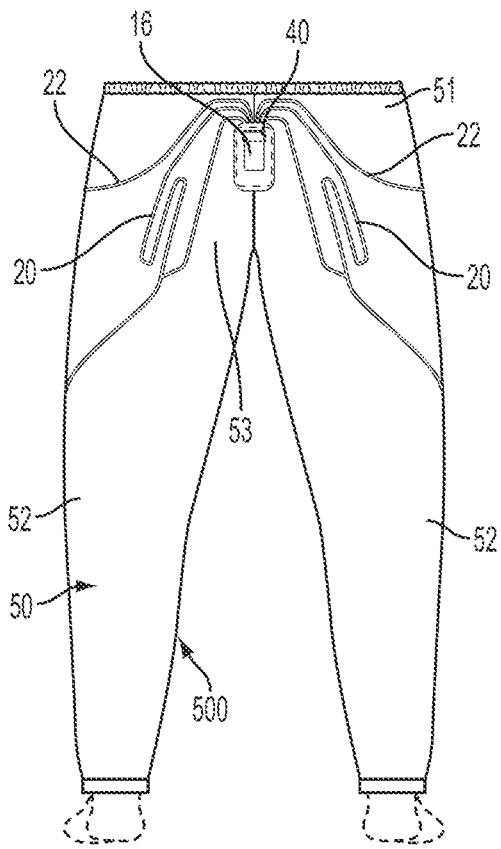
FIG. 9 is a magnified view as shown in FIG. 8, with an alternate housing attached to the pants.
Figure 10:
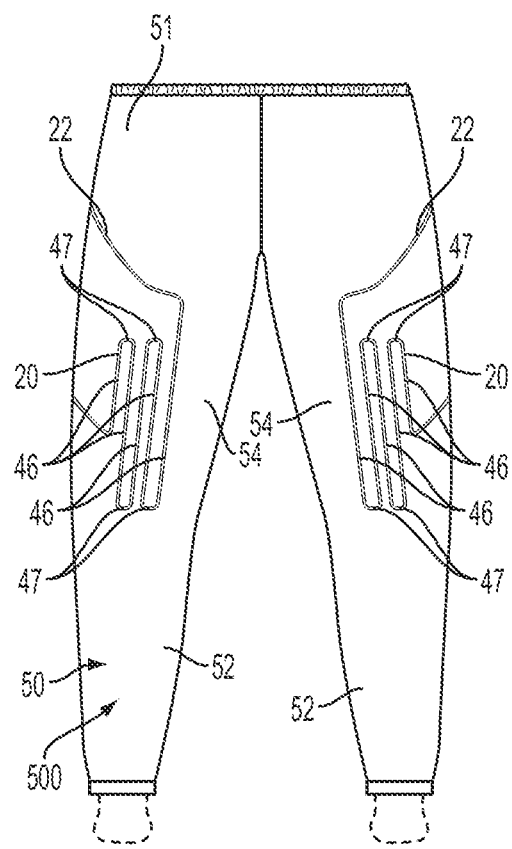
FIG. 10 is a front view of the pants of FIG. 7.

FIGS. 7-10 illustrate another embodiment of an article of apparel 500 that includes a clothing member 50 in the form of pants, having a sensor system 12 connected thereto. The clothing member 50 is configured as pants to be worn on a user's lower body, and as illustrated in FIG. 7, includes a waist portion 51 with legs 52 extending downward from the waist portion 51 and configured to at least partially cover the user's legs. The waist portion 51 has a back region 53 configured to at least partially cover the user's back side, and the legs 52 have knee regions 54 configured to at least partially cover the user's knees. The sensor system 12 includes the same general features as described above with respect to the embodiment of FIGS. 1-6, including sensors 20 and leads 22 connecting the sensors 20 to a port 14, as well as any variations or alternate embodiments. The port 14 may include a housing 40 as described above and shown in FIGS. 1-3 or as shown in FIG. 5, or another type of housing, for holding the electronic module 16, which may be positioned adjacent the port 14. In the embodiment shown in FIGS. 7-10, the port 14 is located in the center of the back region 53 of the clothing member 50 (e.g. in a tailbone area), but may be located elsewhere in other embodiments, such as a hip area or a belt buckle area. Additionally, the clothing member 50 has sensors 20 located in the knee regions 54, which deform upon flexing of the user's knees, and two sensors 20 located in the back region 53, which deform upon raising of the user's knees and thighs. It is understood that the article 500 may include additional sensors 20 and/or sensors 20 in other positions in other embodiments. It is also understood that the clothing member 50 and/or the sensor system 12 may include any variations or alternative configurations described above.

FIGS. 11-12 illustrate another embodiment of an article of apparel 600 that includes a clothing member 60 in the form of a bodysuit, having a sensor system 12 connected thereto. The clothing member 60 is configured as a bodysuit to be worn on to cover a user's full body, and as illustrated in FIGS. 11-12, includes a trunk portion 61 with legs 62 extending downward from the trunk portion 61 configured to at least partially cover the user's legs, as well as sleeves 63 extending from the sides of the trunk portion 61 configured to at least partially cover the user's arms. The trunk portion 61 has a lower back region 64 configured to at least partially cover the user's lower back, back side, and hips, and an upper back region 65 configured to at least partially cover the user's upper back. The legs 62 have knee regions 66 configured to at least partially cover the user's knees. The sleeves 63 have elbow regions 67 configured to at least partially cover the user's elbows. Shoulder regions 68 and underarm regions 69 connect the sleeves 63 to the trunk portion 61 and are configured to at least partially cover the user's shoulders and underarms, respectively. The sensor system 12 includes the same general features as described above with respect to the embodiments of FIGS. 1-10, including sensors 20 and leads 22 connecting the sensors 20 to a port 14, as well as any variations or alternate embodiments. The port 14 may include a housing 40 as described above or another type of housing, for holding the electronic module 16, which may be positioned adjacent the port 14. In the embodiment shown in FIGS. 11-12, the port 14 is located in the center of the upper back region 65 of the clothing member 60, but may be located elsewhere in other embodiments, such as at a lower portion of the trunk portion 61 (e.g. a front or back waist area). Additionally, the clothing member 60 has sensors 20 located in the elbow regions 67, which deform upon flexing of the user's elbows, sensors 20 located in the knee regions 66, which deform upon flexing of the user's knees, and two sensors 20 located in the lower back region 64, which deform upon raising of the user's knees and thighs. Additional sensors 20 are positioned on the back sides of each of the shoulder regions 68 and in each underarm region 69 of the clothing member 60, with leads 22 connecting each sensor 20 to the port 14. These sensors 20 deform when the user's arms are raised and lowered or moved forward and backward. It is understood that the article 600 may include additional sensors 20 and/or sensors 20 in other positions in other embodiments. It is also understood that the clothing member 60 and/or the sensor system 12 may include any variations or alternative configurations described above.

Figure 13:
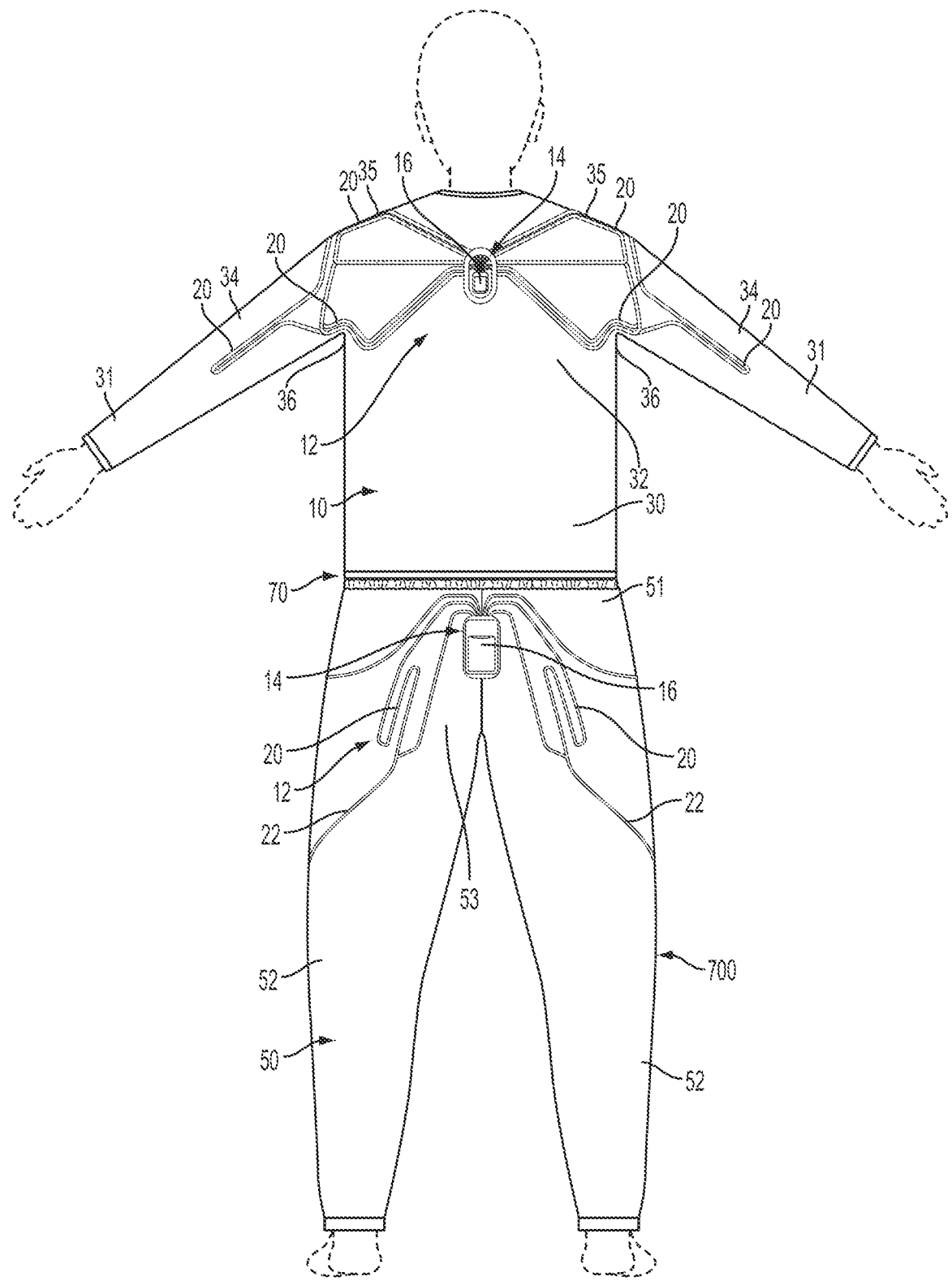
FIG. 13 is a rear view of another embodiment of an article of apparel in the form of a track suit including a shirt as shown in FIG. 1 and pants as shown in FIG. 7.

FIG. 13 illustrates an additional embodiment of an article of apparel 700 including a clothing member 70 in the form of a track suit that includes separate clothing members in the form of a shirt 10 and pants 50 as described above and shown in FIGS. 1-10, having a sensor system 12 connected thereto. In the embodiment of FIG. 13, the article 700 includes two ports 14 with two electronic modules 16 that are arranged and positioned as described above in connection with the clothing members 10, 50 of FIGS. 1-10. The two modules 16 in this embodiment may be configured to communicate simultaneously with a separate electronic device, and may additionally or alternately be configured to communicate with each other. In another embodiment, the article 700 may include a single port 14 connected to a single module 16. The port 14 is positioned in the upper part of the back region 32 of the shirt member 10, similar to the article 600 of FIGS. 11-12, where the leads 22 from the sensors 20 in the pants member 50 extend from the pants member 50 to the shirt member 10. This may be accomplished by the use of a bridging connection, such as a releasable electronic connection, for example any variety of plugs, computer connectors, etc. It is also understood that the clothing member 70 and/or the sensor system 12 may include any variations or alternative configurations described above.

Figure 14:
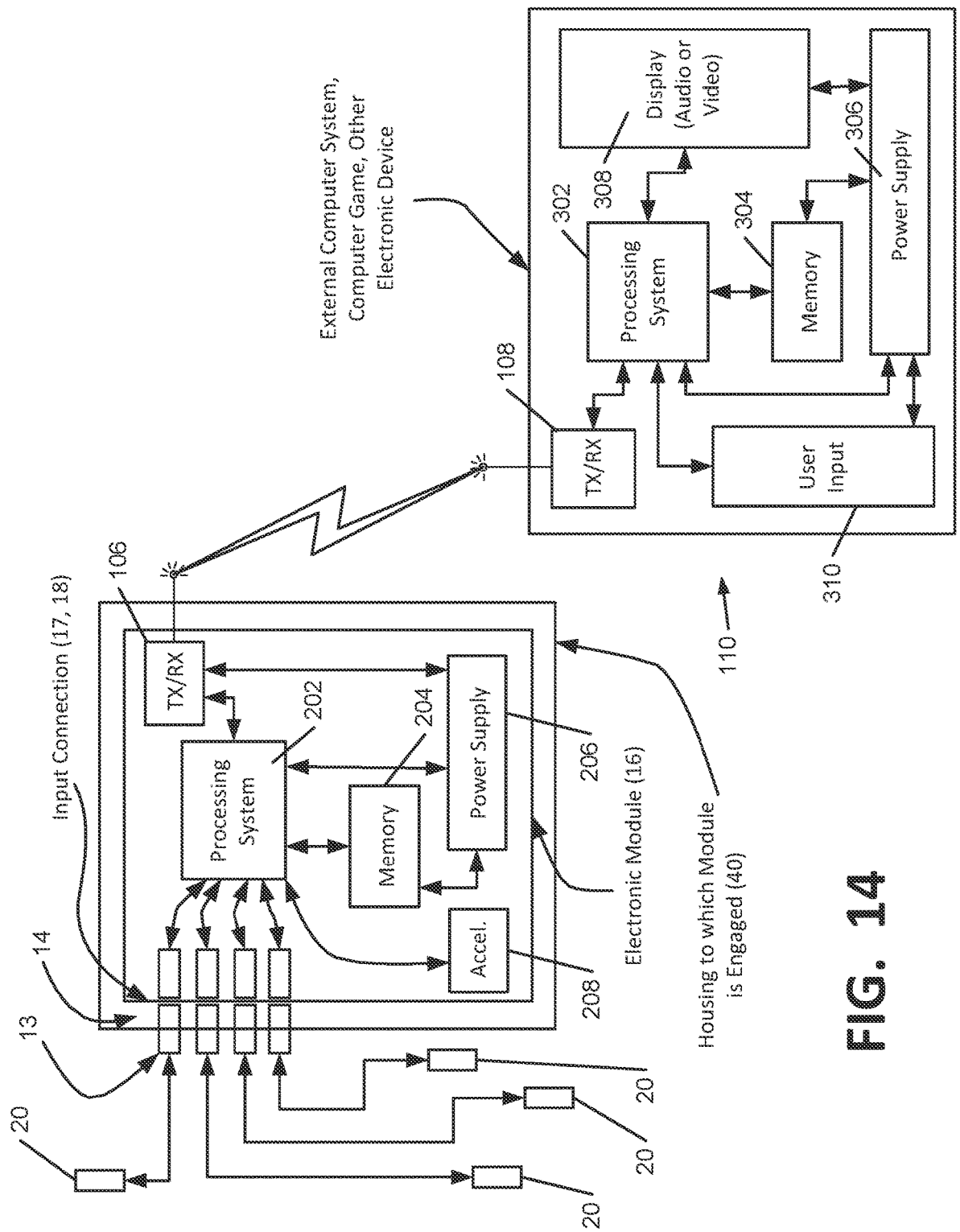
FIG. 14 is a schematic diagram of one embodiment of an electronic module capable of use with a sensor system, in communication with an external electronic device.
Figure 15:
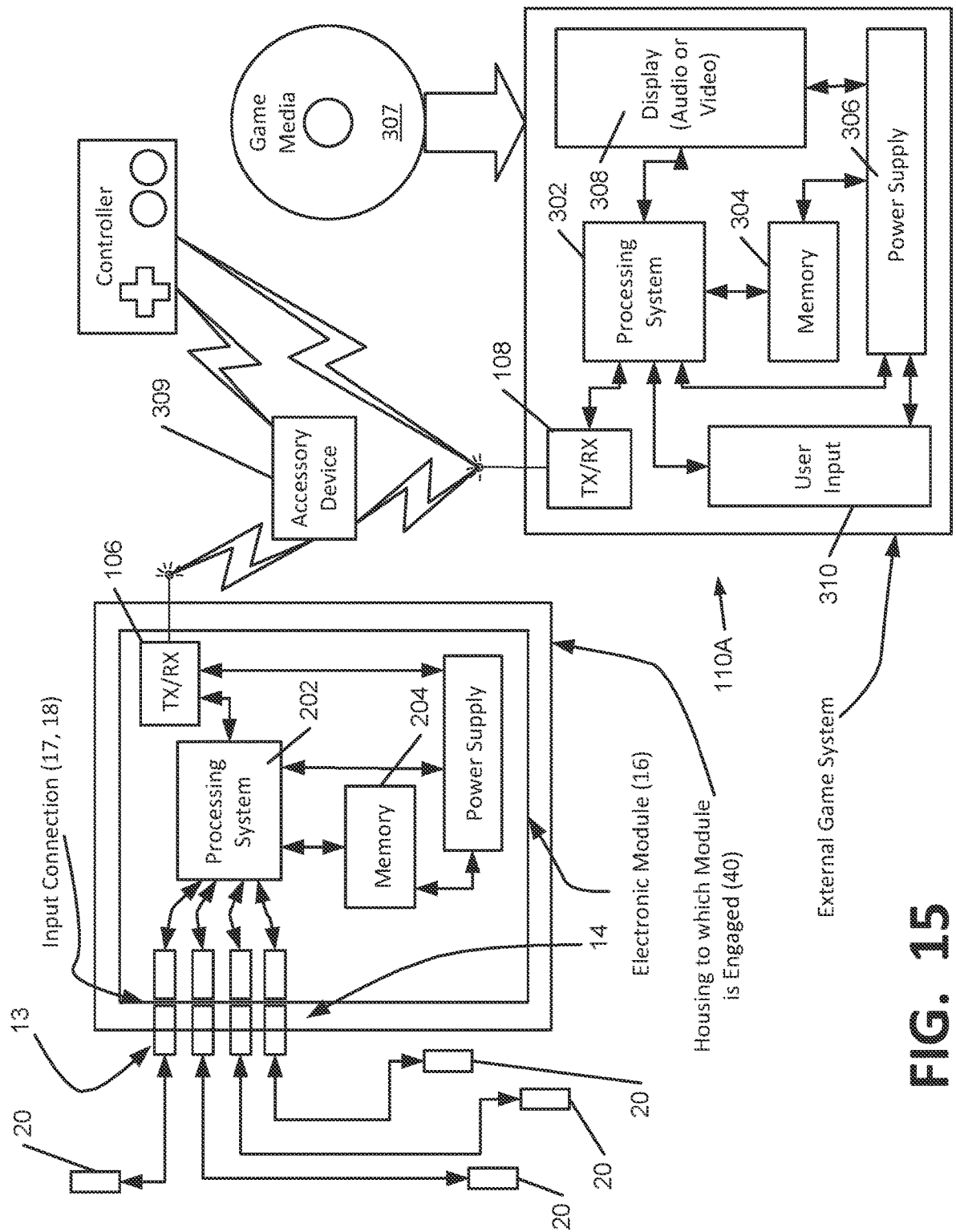
FIG. 15 is a schematic diagram of the electronic module of FIG. 14, in communication with an external gaming device.

The port 14 is configured for communication of data collected by the sensors 20 to an outside source, in one or more known manners. In one embodiment, as shown in FIGS. 14-15, the port 14 is a universal communication port, configured for communication of data in a universally readable format. As described above, in the embodiments shown in FIGS. 1-13, the port 14 includes an interface 18 for connection to an electronic module 16, shown in connection with the port 14 in FIGS. 3 and 14-15. In the embodiment shown in FIGS. 14-15, the interface 18 may take the form of electrical contacts. As also described above the sensor leads 22 in FIGS. 1-13 are consolidated to form the interface 18 at their terminal ends, in order to connect to the port 14, as shown in greater detail in FIG. 4. In one embodiment, leads 22 may be individually connected to the port interface 18, such as through the connection pins 13 discussed above. In another embodiment, the sensor leads 22 could be consolidated to form an external interface, such as a plug-type interface or another configuration, and in a further embodiment, the sensor leads 22 may form a non-consolidated interface, with each lead 22 having its own sub-interface. As illustrated in FIGS. 2, 4-5, and 8-9, the sensor leads 22 can converge to a single location to form the consolidated interface. As also described below, the module 16 may have an interface 17 for connection to the port interface 18 and/or the sensor leads 22.

The port 14 is adapted for connection to a variety of different electronic modules 16, which may be as simple as a memory component (e.g., a flash drive) or which may contain more complex features. It is understood that the module 16 could be as complex a component as a personal computer, mobile device, server, etc. The port 14 is configured for transmitting data gathered by the sensors 20 to the module 16 for storage and/or processing. Although the port 14 is illustrated with electronic contacts forming an interface 18 for connection to a module, in other embodiments, the port 14 may contain one or more additional or alternate communication interfaces. For example, the port 14 may contain or comprise a USB port, a Firewire port, 16-pin port, or other type of physical contact-based connection, or may include a wireless or contactless communication interface, such as an interface for Wi-Fi, Bluetooth, near-field communication, RFID, Bluetooth Low Energy, Zigbee, or other wireless communication technique, or an interface for infrared or other optical communication technique.

The module 16 may additionally have one or multiple communication interfaces for connecting to one or more external devices 110 to transmit the data for processing, as described below and shown in FIG. 14. Such interfaces can include any of the contacted or contactless interfaces described above. In one embodiment, the module 16 is configured for connecting to the external device 110 using a wireless connection technique, such as those mentioned above. In this embodiment, the module 16 may be configured for wireless communication with the external device 110, which allows the device 22 to remain connected to the port 14. In a wireless embodiment, the module 16 may be connected to an antenna for wireless communication. The antenna may be shaped, sized, and positioned for use with the appropriate transmission frequency for the selected wireless communication method. Additionally, the antenna may be located internally within the module 16 or external to the module. Additionally, the module 16 may be configured for contacted or contactless connection to a mobile device, such as a watch, cell phone, portable music player, etc. In another embodiment, the module 16 additionally or alternately includes a physical connector, such as a retractable USB connection for connection to the external device 110. The module 16 may be configured to be removed from the port 14 to be directly connected to the external device 110 for data transfer, such as by the retractable USB connection described above. In one embodiment, the module 16 may be permanently mounted to the clothing member 10, or alternately may be removable at the option of the user and capable of remaining mounted to the clothing member 10 if desired. Additionally, as further explained below, the module 16 may be removed and replaced with another module 16 programmed and/or configured for gathering and/or utilizing data from the sensors 20 in another manner. If the module 16 is permanently mounted to the clothing member 10, the sensor system 12 may further contain an external port to allow for data transfer and/or battery charging, such as a USB or Firewire port. It is understood that the module 16 may be configured for both contacted and contactless communication.

FIG. 14 shows a schematic diagram of an example electronic module 16 including data transmission/reception capabilities through a data transmission/reception system 106, which may be used in accordance with at least some examples of this invention. While the example structures of FIG. 14 illustrate the data transmission/reception system (TX-RX) 106 as integrated into the electronic module structure 16, those skilled in the art will appreciate that a separate component may be included as part of the structure of an article of apparel 100, et seq., or other structure for data transmission/reception purposes and/or that the data transmission/reception system 106 need not be entirely contained in a single housing or a single package in all examples of the invention. Rather, if desired, various components or elements of the data transmission/reception system 106 may be separate from one another, in different housings, on different boards, and/or separately engaged with the article of apparel 100, et seq., or other device in a variety of different manners without departing from this invention. Various examples of different potential mounting structures are described in more detail below.

In the example of FIG. 14, the electronic component 16 may include a data transmission/reception element 106 for transmitting data to and/or receiving data from one or more remote systems. In one embodiment, the transmission/reception element 106 is configured for communication through the port 14, such as by the contacted or contactless interfaces described above. In the embodiment shown in FIG. 14, the module 16 includes an interface 17 configured for connection to the port 14 and/or sensors 20. In the module 16 illustrated in FIG. 14, the interface 17 has contacts that are complementary with the contacts of the interface 18 of the port 14, to connect with the port 14. In other embodiments, as described above, the port 14 and the module 16 may contain different types of interfaces 17, 18, which may be wired or wireless. It is understood that in some embodiments, the module 16 may interface with the port 14 and/or sensors 20 through the TX-RX element 106. Accordingly, in one embodiment, the module 16 may be external to the article 100, et seq., and the port 14 may comprise a wireless transmitter interface for communication with the module 16. The electronic module 16 of this example further includes a processing system 202 (e.g., one or more microprocessors), a memory system 204, and a power supply 206 (e.g., a battery or other power source).

Connection to the one or more sensors can be accomplished through TX-RX element 106, but additional sensors (not shown) may be provided to sense or provide data or information relating to a wide variety of different types of parameters, such as physical or physiological data associated with use of the article 100, et seq., or the user, including pedometer type speed and/or distance information, other speed and/or distance data sensor information, temperature, altitude, barometric pressure, humidity, GPS data, accelerometer output or data, heart rate, pulse rate, blood pressure, body temperature, EKG data, EEG data, data regarding angular orientation and changes in angular orientation (such as a gyroscope-based sensor), etc., and this data may be stored in memory 204 and/or made available, for example, for transmission by the transmission/reception system 106 to some remote location or system. The additional sensor(s), if present, may also include an accelerometer 208 (e.g., for sensing direction changes during steps, such as for pedometer type speed and/or distance information, for sensing jump height, changes of direction, etc.).

An electronic module 16 as shown in FIG. 14 can include an activation system (not shown). The activation system or portions thereof may be engaged with the module 16 or with the article 100, et seq., (or other device) together with or separate from other portions of the electronic module 16. The activation system may be used for selectively activating the electronic module 16 and/or at least some functions of the electronic module 16 (e.g., data transmission/reception functions, etc.). A wide variety of different activation systems may be used without departing from this invention, and a variety of such systems will be described in more detail below with respect to various included figures. In one example, the sensor system 12 may be activated and/or deactivated by activating the sensors 20 in a specific pattern, such as consecutive or alternating arm or leg bends. In another example, the sensor system 12 may be activated by a button or switch, which may be located on the module 16, on the clothing member 10, or on an external device in communication with the sensor system 12, as well as other locations. In any of these embodiments, the sensor system 12 may contain a "sleep" mode, which can deactivate the system 12 after a set period of inactivity. In an alternate embodiment, the sensor system 12 may operate as a low-power device that does not activate or deactivate.

The module 16 may further be configured for communication with an external device 110, as described above, which may be an external computer or computer system, mobile device, gaming system, or other type of electronic device, as shown in FIGS. 14-15. The exemplary external device 110 shown in FIGS. 14-15 includes a processor 302, a memory 304, a power supply 306, a display 308, a user input 310, and a data transmission/reception system 108. The transmission/reception system 108 is configured for communication with the module 16 via the transmission/reception system 106 of the module 16, through any type of known electronic communication, including the contacted and contactless communication methods described above and elsewhere herein. It is understood that the module 16 can be configured for communication with a plurality of external devices, including a wide variety of different types and configurations of electronic devices. Additionally, the transmission/reception system 106 of the module 16 may be configured for a plurality of different types of electronic communication. It is further understood that the shoe 80 may include a separate power source to operate the sensors 20 if necessary, such as a battery, piezoelectric, solar power supplies, or others. The sensors 20 may also simply receive power through connection to the module 16.

The operation and use of the sensor system 12 is described below with respect to the sensor system 12 shown in FIGS. 1-6, and it is understood that the principles of operation of the sensor system 12, including all embodiments and variations thereof, are applicable to the other embodiments of the sensor system 12 described above. In operation, the sensors 20 gather data according to their function and design, and transmit the data to the port 14. The port 14 then allows the electronic module 16 to interface with the sensors 20 and collect the data for later use and/or processing. In one embodiment, the data is collected, stored, and transmitted in a universally readable format, so the data is able to be accessed and/or downloaded by a plurality of users, with a variety of different applications, for use in a variety of different purposes. In one example, the data is collected, stored, and transmitted in XML format.

In different embodiments, the sensor system 12 may be configured to collect different types of data. In one embodiment (described above), the sensor(s) 20 can collect data reflecting movement of the body at the points around the sensors 20, e.g. at the user's joints in one embodiment. For example, the sensors 20 may gradually increase in resistance as the deformation of the sensor 20 changes due to different degrees of flexing or other movement. From this data, information about the user's movements can be gathered, such as the number, sequence, and/or frequency of movement, as well as the degree of movement, the speed of movement, and other information. In another embodiment, the sensors 20 may be binary on/off type sensors, rather than qualitative sensors. Such data may not permit the degree of the user's movement to be detected, but other aspects of the user's movement can be detected, such as number, sequence, frequency, etc. In further embodiments, the sensor(s) 20 may be able to measure rates of changes in flexing, bending, or other deformation, and/or other temporally-dependent parameters. It is understood that, in any embodiment, the sensors 20 may require a certain threshold force or deformation before registering data.

As described above, the data is provided through the universal port 14 to the module 16 in a universally readable format, so that the number of applications, users, and programs that can use the data is nearly unlimited. Thus, the port 14 and module 16 are configured and/or programmed as desired by a user, and the port 14 and module 16 receive input data from the sensor system 12, which data can be used in any manner desired for different applications. In many applications, the data is further processed by the module 16 and/or the external device 110 prior to use. In configurations where the external device 110 further processes the data, the module 16 may transmit the data to the external device 110. This transmitted data may be transmitted in the same universally-readable format, or may be transmitted in another format, and the module 16 may be configured to change the format of the data. Additionally, the module 16 can be configured and/or programmed to gather, utilize, and/or process data from the sensors 20 for one or more specific applications. In one embodiment, the module 16 is configured for gathering, utilizing, and/or processing data for use in a plurality of applications. Examples of such uses and applications are given below. As used herein, the term "application" refers generally to a particular use, and does not necessarily refer to use in a computer program application, as that term is used in the computer arts. Nevertheless, a particular application may be embodied wholly or partially in a computer program application.

Further, the module 16 can be removed from the clothing member and replaced with a second module 16 configured for operating differently than the first module 16. In the embodiment of FIGS. 1-6, the replacement is accomplished by disconnecting the first module 16 from the port 14 and removing the first module 16 from the well 41, then inserting the second module 16 into the well 41 and connecting the second module 16 to the port 14. The second module 16 may be programmed and/or configured differently than the first module 16. In one embodiment, the first module 16 may be configured for use in one or more specific applications, and the second module 16 may be configured for use in one or more different applications. For example, the first module 16 may be configured for use in one or more gaming applications and the second module 16 may be configured for use in one or more athletic performance monitoring applications. Additionally, the modules 16 may be configured for use in different applications of the same type. For example, the first module 16 may be configured for use in one game or athletic performance monitoring application, and the second module 16 may be configured for use in a different game or athletic performance monitoring application. As another example, the modules 16 may be configured for different uses within the same game or performance monitoring application. In another embodiment, the first module 16 may be configured to gather one type of data, and the second module 16 may be configured to gather a different type of data. Examples of such types of data are described herein, including quantitative force measurement, relative force measurement (i.e. sensors 20 relative to each other), weight shifting/transfer, impact sequences (such as for stride patterns) rate of force change, etc. In a further embodiment, the first module 16 may be configured to utilize or process data from the sensors 20 in a different manner than the second module 16. For example, the modules 16 may be configured to only gather, store, and/or communicate data, or the modules 16 may be configured to further process the data in some manner, such as organizing the data, changing the form of the data, performing calculations using the data, etc. In yet another embodiment, the modules 16 may be configured to communicate differently, such as having different communication interfaces or being configured to communicate with different external devices 110. The modules 16 may function differently in other aspects as well, including both structural and functional aspects, such as using different power sources or including additional or different hardware components, such as additional sensors as described above (e.g. GPS, accelerometer, etc.).

One use contemplated for the data collected by the system 12 is in detecting and/or measuring movement by flexing of the user's joints, including joints used in a wide variety of athletic activities, such as elbows, shoulders, knees, and hips. As described above, information about the user's movements that can be gathered from the data include the number, sequence, and/or frequency of movement, the degree of movement, the speed of movement, and other information. It is understood that more or less expensive and complex sensor systems 12 may be designed, based on the intended use of the data collected thereby. The data collected by the system 12 can be used in measurement of a variety of other athletic performance characteristics. For example, speed and distance monitoring can be performed, which may include pedometer-based measurements. As another example, movement information can be used to model the user's movements (such as by an external device 110). Such movements that can be modeled include, without limitation, running form, throwing form (e.g., baseball, football, softball, cricket, etc.), basketball shooting form, swing form (e.g., baseball, golf, tennis, hockey, etc.), kicking form (e.g. soccer or football), ice skating or roller skating form, jumping form, climbing form, weightlifting or other stationary exercise form, posture, and other such movements.

The data, or the measurements derived therefrom, may be useful for athletic training purposes, including improving speed, power, quickness, consistency, technique, etc. The port 14, module 16, and/or external device 110 can be configured to give the user active, real-time feedback. In one example, the port 14 and/or module 16 can be placed in communication with a computer, mobile device, etc., in order to convey results in real time. Additionally, the data can be used to compare athletic movements, such as comparing a movement with a user's past movements to show consistency, improvement, or the lack thereof, or comparing a user's movement with the same movement of another, such as a professional golfer's swing. Further, the system 12 may be used to record biomechanical data for a "signature" athletic movement of an athlete. This data could be provided to others for use in duplicating or simulating the movement, such as for use in gaming applications or in a shadow application that overlays a movement over a user's similar movement.

The system 12 can also be configured for "all day activity" tracking, to record the various activities a user engages in over the course of a day. The system 12 may include a special algorithm for this purpose, such as in the module 16, the external device 110, and/or the sensors 20.

The system 12 may also be used for control applications, rather than data collection and processing applications. In other words, the system 12 could be incorporated into apparel, or another clothing member that encounters bodily contact, for use in controlling an external device 110, such as a computer, television, video game, etc., based on movements by the user detected by the sensors 20. In effect, the apparel with the incorporated sensors 20 and leads 22 extending to a universal port 14 allows the apparel to act as an input system, and the electronic module 16 can be configured, programmed, and adapted to accept the input from the sensors 20 and use this input data in any desired manner, e.g., as a control input for a remote system. For example, a shoe with sensor controls could be used as a control or input device for a computer, or for a program being executed by the computer, similarly to a mouse, where certain movements, gestures, etc. (e.g., a horizontal or vertical hand or arm wave, a kick, etc.) can control a pre-designated operation on a computer (e.g., page down, page up, undo, copy, cut, paste, save, close, etc.). Software can be provided to assign various gestures to different computer function controls for this purpose. It is contemplated that an operating system could be configured to receive and recognize control input from the sensor system 12. Televisions or other external electronic devices can be controlled in this manner. Articles 100, 500, 600, 700 incorporating the system 12 can also be used in gaming applications and game programs, similarly to the Nintendo Wii controller, where specific movements can be assigned certain functions and/or can be used to produce a virtual representation of the user's motion on a display screen. The system 12 can be used as an exclusive controller for a game or other computer system, or as a complementary controller.

Additionally, the system 12 may be configured to communicate directly with the external device 110 and/or with a controller for the external device. As described above, FIG. 14 illustrates one embodiment for communication between the electronic module 16 and the external device. In another embodiment, shown in FIG. 15, the system 12 can be configured for communication with an external gaming device 110A. The external gaming device 110A contains similar components to the exemplary external device 110 shown in FIG. 14. The external gaming device 110A also includes at least one game media 307 containing a game program (e.g. a cartridge, CD, DVD, Blu-Ray, or other storage device), and at least one remote controller 305 configured to communicate by wired and/or wireless connection through the transmitting/receiving element 108. In the embodiment shown, the controller 305 complements the user input 310, however in one embodiment, the controller 305 may function as the sole user input. In this embodiment, the system 12 is provided with an accessory device 309, such as a wireless transmitter/receiver with a USB plug-in, that is configured to be connected to the external device 110 and/or the controller 305 to enable communication with the module 16. In one embodiment, the accessory device 309 may be configured to be connected to one or more additional controllers and/or external devices, of the same and/or different type than the controller 305 and the external device 110. It is understood that if the system 12 includes other types of sensors described above (e.g., an accelerometer), such additional sensors can also be incorporated into controlling a game or other program on an external device 110.

An external device 110, such as a computer/gaming system, can be provided with other types of software to interact with the system 12. For example, a gaming program may be configured to alter the attributes of an in-game character based on a user's real-life activities, which can encourage exercise or greater activity by the user. In another example, a program may be configured to display an avatar of the user that acts in relation or proportion to the user activity collected by the sensing system of the shoe. In such a configuration, the avatar may appear excited, energetic, etc., if the user has been active, and the avatar may appear sleepy, lazy, etc., if the user has been inactive. The sensor system 12 could also be configured for more elaborate sensing to record data describing a "signature move" of an athlete, which could then be utilized for various purposes, such as in a gaming system or modeling system.

A single article 100, et seq., containing the sensor system 12 as described herein can be used alone or in combination with a second article 100, et seq., having its own sensor system 12, such as the articles 100, 500 in the track suit 70 illustrated in FIG. 13 and described above. In one embodiment, one of the articles 100, et seq., described above may have a sensor system 12 that communicates or otherwise works in conjunction with a sensor system 82 in an article of footwear 80, as illustrated in FIG. 20, where the sensor system 82 of the footwear 80 is in communication with the sensor system 12 of the shirt article 100. In the embodiment of FIG. 20, the article of footwear 80 has a sensor system 82 that includes a port 81, one or more sensors 83 connected to the port 81, and a module 84 connected to the port 81 to receive data from the sensors 83. The sensor system 82 of the article of footwear 80 may utilize FSR sensors, and may be configured according to one or more embodiments as described in U.S. patent application Ser. No. 13/401,918, which application is incorporated by reference herein in its entirety and made part hereof. Additional embodiments of sensors and sensor systems, as well as articles of footwear and sole structures and members utilizing the same, are described in U.S. patent application Ser. No. 12/483,824, published as U.S. Patent Application Publication No. 2010/0063778; U.S. patent application Ser. No. 12/483,828, published as U.S. Patent Application Publication No. 2010/0063779; and U.S. patent application Ser. Nos. 13/399,778 and 13/399,935, all of which applications are incorporated by reference herein in their entireties and made part hereof. FIG. 20 illustrates the modules 16, 84 in communication with each other, and it is understood that one or more intermediate devices may be involved in such communication. In one embodiment, the data from the sensor system 12 in the article of apparel 100 can be integrated, combined, and/or otherwise used together with the data from the sensor system 82 of the footwear 80. Such integrated data can provide further detail describing the user's movement, and can be used in any of the applications described herein or in the aforementioned patent applications, as well as other uses. The data integration can be performed by a module 16, 84 or may be performed by an external device 110, after receiving the data from both the sensor systems 12, 82. The device 110 may also generate visual, audio, or other output of the integrated data, which may include performance indicators.

Various modes of communication may be used to integrate the data from multiple sensor systems 12, 82, including any modes of communication described in the aforementioned patent applications may be used as well. As illustrated in FIG. 20, the module 16 of the sensor system 12 may communicate directly with the module 84 of the footwear sensor system 82 and/or both modules 16, 84 may communicate with an external device 110 in one embodiment. In another embodiment, only a single module 16 may be used for both sensor systems 12, 82. For example, the port 14 of the apparel sensor system 12 or the port 81 of the footwear sensor system 82 may be configured for wireless communication with the module 16 to enable such use. As another example, one or more individual sensors 20, 83 of the sensor systems 12, 82 may have a dedicated antenna or other communication device for communication with other components and/or devices described herein. Still other uses and applications of the data collected by the system 12 are contemplated within the scope of the invention and are recognizable to those skilled in the art.

As will be appreciated by one of skill in the art upon reading the present disclosure, various aspects described herein may be embodied as a method, a data processing system, or a computer program product. Accordingly, those aspects may take the form of an entirely hardware embodiment, an entirely software embodiment or an embodiment combining software and hardware aspects. Furthermore, such aspects may take the form of a computer program product stored by one or more tangible computer-readable storage media or storage devices having computer-readable program code, or instructions, embodied in or on the storage media. Any suitable tangible computer readable storage media may be utilized, including hard disks, CD-ROMs, optical storage devices, magnetic storage devices, and/or any combination thereof. In addition, various intangible signals representing data or events as described herein may be transferred between a source and a destination in the form of electromagnetic waves traveling through signal-conducting media such as metal wires, optical fibers, and/or wireless transmission media (e.g., air and/or space).

As described above, aspects of the present invention may be described in the general context of computer-executable instructions, such as program modules, being executed by a computer and/or a processor thereof. Generally, program modules include routines, programs, objects, components, data structures, etc. that perform particular tasks or implement particular abstract data types. Such a program module may be contained in a tangible computer-readable medium, as described above. Aspects of the present invention may also be practiced in distributed computing environments where tasks are performed by remote processing devices that are linked through a communications network. Program modules may be located in a memory, such as the memory 204 of the module 16 or memory 304 of the external device 110, or an external medium, such as game media 307, which may include both local and remote computer storage media including memory storage devices. It is understood that the module 16, the external device 110, and/or external media may include complementary program modules for use together, such as in a particular application. It is also understood that a single processor 202, 302 and single memory 204, 304 are shown and described in the module 16 and the external device 110 for sake of simplicity, and that the processor 202, 302 and memory 204, 304 may include a plurality of processors and/or memories respectively, and may comprise a system of processors and/or memories.

The various embodiments of the sensor system described herein, as well as the articles of apparel and other structures incorporating the sensor system, provide benefits and advantages over existing technology. For example, many of the sensor embodiments described herein provide relatively low cost and durable options for sensor systems, so that a sensor system can be incorporated into articles of apparel with little added cost and good reliability. As a result, apparel can be manufactured with integral sensor systems regardless of whether the sensor systems are ultimately desired to be used by the consumer, without appreciably affecting price. Additionally, the article(s) of apparel may be manufactured as thin and lightweight garments to be worn underneath a user's normal apparel, providing performance tracking without affecting the user's external appearance and style. As another example, the sensor system provides a wide range of functionality for a wide variety of applications, including gaming, fitness, athletic training and improvement, practical controls for computers and other devices, and many others described herein and recognizable to those skilled in the art. In one embodiment, third-party software developers can develop software configured to run using input from the sensor systems, including games and other programs. The ability of the sensor system to provide data in a universally readable format greatly expands the range of third party software and other applications for which the sensor system can be used.

Several alternative embodiments and examples have been described and illustrated herein. A person of ordinary skill in the art would appreciate the features of the individual embodiments, and the possible combinations and variations of the components. A person of ordinary skill in the art would further appreciate that any of the embodiments could be provided in any combination with the other embodiments disclosed herein. It is understood that the invention may be embodied in other specific forms without departing from the spirit or central characteristics thereof. The present examples and embodiments, therefore, are to be considered in all respects as illustrative and not restrictive, and the invention is not to be limited to the details given herein. The terms "first," "second," "top," "bottom," etc., as used herein, are intended for illustrative purposes only and do not limit the embodiments in any way. Additionally, the term "plurality," as used herein, indicates any number greater than one, either disjunctively or conjunctively, as necessary, up to an infinite number. Further, "Providing" an article or apparatus, as used herein, refers broadly to making the article available or accessible for future actions to be performed on the article, and does not connote that the party providing the article has manufactured, produced, or supplied the article or that the party providing the article has ownership or control of the article. Accordingly, while specific embodiments have been illustrated and described, numerous modifications come to mind without significantly departing from the spirit of the invention and the scope of protection is only limited by the scope of the accompanying Claims.

What is claimed is:

1. An athletic performance monitoring system comprising:
    an article of apparel configured to be worn on a body of a user, the article of apparel comprising an upper body portion configured to be worn on an upper body of the user and a lower body portion configured to be worn on a lower body of the user;
    a sensor system connected to the article of apparel and configured to sense a movement of the user, the sensor system comprising an upper body sensor connected to the upper body portion of the article of apparel, a lower body sensor connected to the lower body portion of the article of apparel, at least one port in communication with the upper body sensor and the lower body sensor, and a plurality of conductive leads connecting the upper body sensor and the lower body sensor to the at least one port, wherein the upper body sensor and the lower body sensor are stretch-based sensors configured to increase in resistance upon tensile deformation, and the conductive leads are configured to conduct electronic signals in any state of deformation;
    at least one electronic module configured for connection to the at least one port and comprising at least one of a memory and a processor, wherein the at least one electronic module is configured for collecting movement data from the upper body sensor and the lower body sensor through the at least one port based on the movement of the user, and wherein the at least one electronic module is further configured for transmitting the movement data; and
    an external device configured for receiving the movement data from the at least one electronic module, the external device further configured for analyzing the movement data and providing real-time feedback to the user regarding the movement of the user, based on analysis of the movement data.

2. The athletic performance monitoring system of claim 1, wherein the at least one electronic module is configured for processing the movement data prior to transmitting the movement data.

3. The athletic performance monitoring system of claim 1, wherein the at least one port comprises at least one housing configured for receiving the at least one electronic module to removably connect the at least one electronic module to the at least one port.

4. The athletic performance monitoring system of claim 1, wherein the external device is configured for analyzing the movement data by comparing the movement data to second movement data related to a second movement, and the real-time feedback comprises an indication of a comparison between the movement of the user and the second movement.

5. The athletic performance monitoring system of claim 1, wherein the article of apparel is a bodysuit, and the upper body portion and the lower body portion are portions of the bodysuit.

6. The athletic performance monitoring system of claim 1, wherein the upper body portion and the lower body portion of the article of apparel are separate articles.

7. The athletic performance monitoring system of claim 1, wherein:
    the at least one port comprises a first port in communication with the upper body sensor and a second port in communication with the lower body sensor; and
    the at least one electronic module comprises a first electronic module configured for connection to the first port and configured for collecting movement data from the upper body sensor through the first port, and a second electronic module configured for connection to the second port and configured for collecting movement data from the lower body sensor through the second port.

8. The athletic performance monitoring system of claim 1, wherein the upper body sensor and the lower body sensor are each formed of a polymeric material having a conductive particulate material dispersed therein at a first dispersion density, wherein the upper body sensor and the lower body sensor are each configured to increase in resistance when deformed under pressure.

9. The athletic performance monitoring system of claim 8, wherein the conductive leads are formed of the polymeric material having the conductive particulate material dispersed therein at a second dispersion density, wherein the second dispersion density is higher than the first dispersion density, such that the plurality of leads have sufficient conductivity to conduct the electronic signals in any state of deformation.

10. The athletic performance monitoring system of claim 1, wherein the external device is a mobile device having a video display and an audio output, wherein the external device is configured for providing the real-time feedback via the video display and/or the audio output.

11. The athletic performance monitoring system of claim 1, wherein the external device is configured for providing the real-time feedback to the user by transmitting the real-time feedback to a second external device configured to provide the real-time feedback to the user.

12. An athletic performance monitoring system comprising:
- an article of apparel configured to be worn on a body of a user, the article of apparel comprising an upper body portion configured to be worn on an upper body of the user and a lower body portion configured to be worn on a lower body of the user;
- a sensor system connected to the article of apparel and configured to sense a movement of the user, the sensor system comprising an upper body sensor connected to the upper body portion of the article of apparel, a lower body sensor connected to the lower body portion of the article of apparel, at least one port in communication with the upper body sensor and the lower body sensor, and a plurality of conductive leads connecting the upper body sensor and the lower body sensor to the at least one port, wherein the upper body sensor and the lower body sensor are stretch-based sensors configured to increase in resistance upon tensile deformation, and the conductive leads are configured to conduct electronic signals in any state of deformation; and
- at least one electronic module configured for connection to the at least one port and comprising at least one of a memory and a processor, wherein the at least one electronic module is configured for collecting movement data from the upper body sensor and the lower body sensor through the at least one port based on the movement of the user, and wherein the at least one electronic module is further configured for analyzing the movement data and providing real-time feedback to the user regarding the movement of the user, based on analysis of the movement data.

13. The athletic performance monitoring system of claim 12, wherein the at least one port comprises at least one housing configured for receiving the at least one electronic module to removably connect the at least one electronic module to the at least one port.

14. The athletic performance monitoring system of claim 12, wherein the at least one electronic module is configured for analyzing the movement data by comparing the movement data to second movement data related to a second movement, and the real-time feedback comprises an indication of a comparison between the movement of the user and the second movement.

15. The athletic performance monitoring system of claim 12, wherein the article of apparel is a bodysuit, and the upper body portion and the lower body portion are portions of the bodysuit.

16. The athletic performance monitoring system of claim 12, wherein the upper body portion and the lower body portion of the article of apparel are separate articles.

17. The athletic performance monitoring system of claim 12, wherein:
- the at least one port comprises a first port in communication with the upper body sensor and a second port in communication with the lower body sensor; and
- the at least one electronic module comprises a first electronic module configured for connection to the first port and configured for collecting movement data from the upper body sensor through the first port, and a second electronic module configured for connection to the second port and configured for collecting movement data from the lower body sensor through the second port.

18. The athletic performance monitoring system of claim 12, wherein the upper body sensor and the lower body sensor are each formed of a polymeric material having a conductive particulate material dispersed therein at a first dispersion density, wherein the upper body sensor and the lower body sensor are each configured to increase in resistance when deformed under pressure.

19. The athletic performance monitoring system of claim 18, wherein the conductive leads are formed of the polymeric material having the conductive particulate material dispersed therein at a second dispersion density, wherein the second dispersion density is higher than the first dispersion density, such that the plurality of leads have sufficient conductivity to conduct the electronic signals in any state of deformation.

20. The athletic performance monitoring system of claim 12, wherein the at least one electronic module is configured for providing the real-time feedback to the user by transmitting the real-time feedback to an external device configured to provide the real-time feedback to the user.

* * * * *